United States Patent [19]

Nugent et al.

[11] Patent Number: 5,952,377
[45] Date of Patent: Sep. 14, 1999

[54] FATTY ACID ANALOGS AND PRODRUGS

[75] Inventors: Sean T. Nugent, Grayslake; Richard A. Mueller, Glencoe, both of Ill.

[73] Assignee: G. D. Searle & Co., Chicago, Ill.

[21] Appl. No.: 09/175,740

[22] Filed: Oct. 20, 1998

Related U.S. Application Data

[60] Division of application No. 09/049,237, Mar. 27, 1998, Pat. No. 5,859,052, which is a continuation-in-part of application No. 08/743,100, Nov. 4, 1996, Pat. No. 5,744,631, which is a continuation of application No. 08/410,450, Mar. 24, 1995, Pat. No. 5,599,947, which is a continuation-in-part of application No. 08/004,370, Jan. 14, 1993, abandoned.

[51] Int. Cl.$^6$ .................. A61K 31/16; C07C 235/06; C07D 233/04; C07D 257/04
[52] U.S. Cl. .................. 514/512; 514/519; 514/520; 514/613; 514/637; 548/253; 548/338.1; 548/483; 548/491; 554/35; 554/42; 554/103; 554/113; 560/39; 560/40
[58] Field of Search .................. 554/35, 42; 514/613, 514/512; 560/39, 40

[56] References Cited

U.S. PATENT DOCUMENTS

| | | |
|---|---|---|
| 5,073,571 | 12/1991 | Heuckeroth et al. .................. 514/557 |
| 5,082,967 | 1/1992 | Heuckeroth et al. .................. 562/512 |
| 5,599,947 | 2/1997 | Nugent et al. . |
| 5,670,650 | 9/1997 | Nugent et al. . |
| 5,672,769 | 9/1997 | Nugent et al. . |
| 5,719,290 | 2/1998 | Nugent et al. . |
| 5,744,631 | 4/1998 | Nugent et al. . |

FOREIGN PATENT DOCUMENTS

| | | |
|---|---|---|
| 499521 | 2/1981 | European Pat. Off. . |
| 327523 | 2/1989 | European Pat. Off. ...... C07C 59/125 |
| 396526 | 4/1990 | European Pat. Off. ...... C07C 226/32 |
| 480901 | 10/1991 | European Pat. Off. ...... C07C 247/04 |
| 2657259 | 7/1991 | France . |
| 62-255810 | 10/1987 | Japan .......................... A61K 37/07 |
| 62-126384 | 3/1989 | Japan . |
| 93/21191 | 10/1993 | WIPO ............................. C07F 9/10 |

OTHER PUBLICATIONS

Towler et al., Rev. Biochem. 57, 69–99 (1988).
Bryant et al., Proc. Natl. Acad. Sci. USA 86, 8655–8659 (1989).
Bryant & Ratner, Proc. Natl. Acad. Sci. USA 87, 523–527 (1991).
Doering et al., Science 252, 1851–1854 (1991).
Bryant et al., Proc. Natl. Acad. Sci. USA 88, 2055–2059 (1991).
Devadas et al., J. Biol. Chem. 267, 7224–7239 (1991).

*Primary Examiner*—Johann Richter
*Assistant Examiner*—Taofiq A. Solola
*Attorney, Agent, or Firm*—Scott J. Meyer

[57] ABSTRACT

Novel derivatives of fatty acid analogs that have from one to three heteroatoms in the fatty acid moiety which can be oxygen, sulfur or nitrogen, are disclosed in which the carboxy-terminus has been modified to form various amides, esters, ketones, alcohols, alcohol esters and nitriles thereof, and are useful as substrates for N-myristoyltransferase (NMT) and/or its acyl coenzyme, as anti-viral and anti-fungal agents or pro-drugs of such agents.

4 Claims, No Drawings

FATTY ACID ANALOGS AND PRODRUGS

This is a division of application Ser. No. 09/049,237, filed Mar. 27, 1998, now U.S. Pat. No. 5,859,052 which is a continuation-in-part of application Ser. No. 08/743,100, filed Nov. 4, 1996, now U.S. Pat. No. 5,744,631, which is a continuation of application Ser. No. 08/410,450, filed Mar. 24, 1995, now U.S. Pat. No. 5,599,947, which is a continuation-in-part of application Ser. No. 08/004,370, filed Jan. 14, 1993, now abandoned.

BACKGROUND OF THE INVENTION

This invention relates to novel compounds and, more particularly, to novel derivatives of fatty acid analogs that have from one to three heteroatoms in the fatty acid moiety which can be oxygen, sulfur or nitrogen, and in which the carboxy-terminus has been modified to form, e.g., various amides, esters, ketones, alcohols, alcohol esters and nitriles thereof.

These novel compounds are useful as anti-viral and anti-fungal agents or pro-drugs of such agents and are particularly useful as inhibitors of retroviruses, especially lentiviruses such as the human immunodeficiency virus (HIV).

The fatty acid acylation of specific eukaryotic proteins is a well-established process. See, e.g., the review article by Towler et al., *Ann. Rev. Biochem.* 57, 69–99 (1988), and references cited therein.

Fatty acid analogs containing heteroatom replacements of methylene groups in the fatty acid chain by oxygen, sulfur and nitrogen have been shown to have various anti-viral and antifungal activity. See, e.g., Bryant et al., *Proc. Natl. Acad. Sci. USA* 86, 8655–8659 (1989);

Bryant and Ratner, *Proc. Natl. Acad. Sci. USA* 87, 523–527 (1991);

Doering et al., *Science* 252, 1851–1854 (1991);

Bryant et al., *Proc. Natl. Acad. Sci. USA* 88, 2055–2059 (1991);

and Devadas et al., *J. Biol. Chem.* 267, 7224–7239 (1992). See also,

U.S. Pat. Nos. 5,073,571; 5,082,967; 5,151,445;

and EPO published patent applications EP 327,523 and EP 480,901.

In French Patent application 2,657,259, N-myristoyl-(S)-phenylalanine is disclosed as an inhibitor of NMT for treatment of cancer and retroviral infection, e.g. AIDS. Antiviral myristoyl-glycine is disclosed in Japanese Patent applications 62-126384 and 62-255810. These reported myristoylamino acids do not contain heteroatoms in the myristic acid moiety.

BRIEF DESCRIPTION OF THE INVENTION

In accordance with the present invention, novel derivatives of fatty acid analogs that have from one to three heteroatoms in the fatty acid moiety which can be oxygen, sulfur or nitrogen, are provided in which the carboxy-terminus is modified to form various amides, esters, ketones, alcohols, alcohol esters and nitriles thereof. These novel compounds can be represented by the following general structural Formula I:

GENERAL STRUCTURE $$A\text{-}Alk_1\text{-}B\text{-}Alk_2\text{-}C\text{-}Alk_3(W)\text{-}Y \quad (I)$$

wherein

A=H, $N_3$, CN, SH, OH, tetrazolyl, triazoyl,

B=O, $NR_8$, $S(O)_m$, lower alkylene,

C=O, $NR_8$, $S(O)_m$, lower alkylene, $Alk_1$=lower alkylene, branched or unbranched, $Alk_2$=lower alkylene, branched or unbranched, $Alk_3$=lower alkylene, branched or unbranched or W substituted lower alkylene, Y=COCl, $CONRR_1$, CO—AA—$OR_3$, $CONR_2$—AA—$OR_3$, $CO_2R_4$, $COR_5$, CN, $CH_2OH$, $CSNH_2$, $CH_2O_2CR_6$,

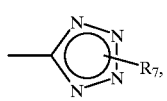

and wherein m=0–2,

W=OZ, halogen, $NR_8$, alkyl, aryl, arylalkyl,

Z=H, alkanoyl, aroyl, arylalkanoyl, wherein

R=H, alkyl, aryl, arylalkyl, $R_1$=H, alkyl, aryl, arylalkyl, $R_2$=H, alkyl, aryl, arylalkyl, $R_3$=H, alkyl, aryl, arylalkyl, $R_4$=H, alkyl, aryl, arylalkyl, $R_5$=alkyl, aryl, arylalkyl, $R_6$=alkyl, aryl, arylalkyl, $R_7$=H, alkyl, aryl, arylalkyl, and $R_8$=H, alkyl, aryl, arylalkyl, AA=D, L, DL or achiral amino acid side chain, and provided that when Y=$CO_2R_4$, $R_4$ is aryl or arylalkyl, and provided further that at least one of B or C contains a N, O or S heteroatom.

In the foregoing general structural Formula I, the lower alkylene groups in each of B, C, $Alk_1$, $Alk_2$ and $Alk_3$ can independently contain from one to about 6 carbon atoms but the total number of carbon atoms in the fatty acid chain when B and C are each alkylene preferably should be 11 or 12.

When B and/or C are any of the heteroatoms O, S(O), and $NR_8$, each of these heteroatoms replaces a methylene group in the fatty acid chain.

The alkyl moieties in any of the R to $R_8$ groups preferably contain from 1 to 12 carbon atoms whereas the aryl and arylalkyl moieties in any of the R to R, groups preferably contain from 6 to 12 carbon atoms.

The alkyl and alkylene groups can be saturated or unsaturated. By the term (W) is meant a side chain on $Alk_3$. The preferred halogens of this side chain are chlorine, bromine and fluorine.

Three preferred groups of compounds of the above general structural Formula I are as follows:

A compound of Formula I in which

A=H, $Alk_1$=$CH_2$, (GROUP A)

B=O and

Alk$_2$-C-Alk$_3$(W)=(CH$_2$)$_{11}$;

A compound of Formula I in which

A=H,

Alk$_1$=CH$_2$, (GROUP B)

B=O,

Alk$_2$=(CH$_2$)$_7$,

C=O and

Alk$_3$(W)=(CH$_2$)$_3$.

A compound of Formula I in which

A=H,

Alk$_1$=(CH$_2$)$_{10}$, (GROUP C)

B=O and

Alk$_2$-C-Alk$_3$(W)=(CH$_2$)$_2$.

When Y contains a AA—OR$_3$ group, AA can be a D, L, L or achiral natural or unnatural alpha-amino acid or natural or unnatural amino acid with the basic amine displaced further from the

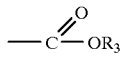

function.

These amino acids can be, for example, any of the approximately 20 natural amino acids that commonly occur in proteins as follows:

| L-Alanine | L-Asparagine | L-Arginine | L-Aspartic acid |
|---|---|---|---|
| L-Cystine | L-Cysteine | L-Glutamic acid | L-Glutamine |
| Glycine | L-Histidine | Hydroxylysine | 4-Hydroxy-L-proline |
| L-Isoleucine | L-Leucine | L-Lysine | L-Methionine |
| L-Phenylalanine | L-Proline | L-Serine | L-Threonine |
| L-Thyroxine | L-Tryptophan | L-Tyrosine | L-Valine |

Amino acids have a primary amino function and a carboxyl function joined to the same carbon atom. Thus, they are called α-amino acids and are derivatives of the general structure NH$_2$—CHR—COOH, in which R can be H or various aliphatic and/or aryl groups. Two exceptions in this list of natural amino acids are L-proline and 4-hydroxyl-L-proline, which are α-imino acids.

β-Amino acids also are commonly known. They have an amino group attached to the carbon one removed from the carboxyl carbon. The nitrogen atom of β-amino acids, as in the case with α-amino acids, can be alkylated.

These naturally occurring and commonly known amino acids can be classified into various groups, illustrated hereinafter such as, e.g., those which have:

(1) aliphatic side chains, (2) hydroxylic side chains, (3) carboxylic side chains and their amides, (4) basic side chains, (5) aromatic side chains, (6) sulfur-containing side chains, and (7) the imino acids.

These amino acids can also be employed herein in the D-configuration as illustrated, for example, by the following:

D-Alanine
D-Isoleucine
D-Phenylalanine
D-Glutamic acid
D-Lysine
D-Tryptophan
D-Threonine Likewise, DL-mixtures of any of these amino acids can be used herein.

Less common amino acids which can be used herein are illustrated by:

β-Alanine (3-Aminopropionic acid)
Homocystine (4,4'-Dithiobis[2-amino-butanoic acid])
Norleucine (2-Aminohexanoic acid)
Norvaline (2-Aminovaleric acid)
Ornithine (2,5-Diaminopentanoic acid)
Penicillamine (3-Mercapto-D-valine)
Phenylglycine and N-Phenylglycine
Sarcosine (N-Methylglycine)
Taurine (2-Aminoethanesulfonic acid)

All of the illustrative amino acids are commercially available and/or can be readily isolated or synthesized by well-known published methods. See, e.g., Williams, *Synthesis of Optically Active α-Amino Acids*, Vol. 7 in organic Chemistry Series, Eds. Baldwin and Magnus, Pergammon Press, 1989. Their chemical structures are also well known as can be seen, e.g., from conventional texts such as Mahler & Cordes, *Biological Chemistry*, Harper & Row, 1966, pp. 8–15; Fieser and Fieser, *Advanced organic Chemistry*, Reinhold Publ. Corp., 1962, pp. 1014–1034; and *The Merck Index*, Eleventh Edition, 1989.

In the general structure of the compounds of Formula I, the N-terminus of the amino acid moiety is bound to the carboxy-terminus of the heteroatom-containing fatty acid moiety. The carboxy-terminus of the amino acid moiety, in turn, is derivatized to form various amides, esters, ketones, alcohols, alcohol esters and nitriles. The compounds of Formula I which thus contain an amino acid moiety can be represented by the following structural Formula II:

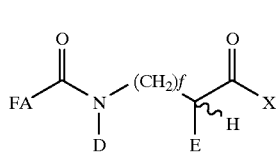

(II)

wherein:

FA is a heteroatom-containing fatty acid moiety selected from the group consisting of CH$_3$O(CH$_2$)$_{11}$— and CH$_3$(CH$_2$)$_9$O(CH$_2$)$_2$—;

f is zero or one;

X is selected from the group consisting of OH, O-alkyl having from one to six carbon atoms, and N(R$_1$)R in which R and R$_1$ are H or alkyl having from one to six carbon atoms or arylalkyl having from one to eight carbon atoms;

D is selected from the group consisting of H, alkyl, aryl, arylalkyl and carboxyalkyl;

E is selected from the group consisting of H. alkyl, aryl, arylalkyl, heteroarylalkyl, arylalkyl substituted with OH or halogen, benzofused heteroarylalkyl, hydroxyalkyl, alkoxyalkyl, arylalkoxyalkyl, thioalkyl, alkylthioalkyl, arylalkylthioalkyl, carboxyalkyl, carboxamidoalkyl, aminoalkyl, aminohydroxyalkyl, diaminoalkyl and guanidinoalkyl;

and in which the number of carbon atoms in each of D and E is from zero to eight.

In the above Formula II, the E groups are illustrated hereinbelow with amino acids as follows:

H is illustrated in glycine;

Alkyl is illustrated in alanine, isoleucine, leucine and valine;

Aryl is illustrated in phenylglycine;

Arylalkyl is illustrated in phenylalanine;

Arylalkyl substituted with OH or halogen is illustrated in tyrosine and fluorophenylalanine;

Heteroarylalkyl (including benzofused) is illustrated in histidine and tryptophane;

Hydroxyalkyl is illustrated in serine and threonine;

Alkoxyalkyl and arylalkoxyalkyl are illustrated in O-methylserine, O-benzylserine and O-benzylthreonine;

Thioalkyl is illustrated in cysteine and its disulfide dimer cystine;

Alkylthioalkyl and arylalkylthioalkyl are illustrated in methionine and S-benzylcysteine;

Carboxyalkyl is illustrated in aspartic acid and glutamic acid;

Carboxamidoalkyl is illustrated in glutamine and asparagine;

Aminoalkyl is illustrated in lysine, N-(O-benzyl)-carbamoyllysine and N-(O-orthochlorobenzyl)-carbamoyllysine;

Amino-hydroxyalkyl is illustrated in hydroxylysine;

Diaminoalkyl is illustrated in aminolysine and ornithine; and

Guanidinoalkyl is illustrated by arginine and N'-toluenesulfonylarginine.

In the above Formula II, the D groups are illustrated hereinbelow with amino acids as follows:

H is illustrated in glycine (Gly);

Alkyl is illustrated in N—(CH$_3$)-Gly-Aryl is illustrated in N—(Ph)-Gly;

Arylalkyl is illustrated in N—(Bn)-Gly; and

Carboxyalkyl is illustrated in N—(Gly-OEt)-Gly;

wherein Ph is phenyl and Bn in benzyl.

For convenience in depicting representative compounds within the scope of Formula II, the amino acid moiety, R, can be shown by the conventional three letter abbreviations of the amino acid as follows:

| Abbreviated Designation | Amino Acid |
|---|---|
| Ala | Alanine |
| Cys | Cysteine |
| Asp | Aspartic acid |
| Glu | Glutamic acid |
| Phe | Phenylalanine |
| Gly | Glycine |
| His | Histidine |
| Ile | Isoleucine |
| Lys | Lysine |
| Leu | Leucine |
| Met | Methionine |
| Asn | Asparagine |
| Pro | Proline |
| Gln | Glutamine |
| Arg | Arginine |
| Ser | Serine |
| Thr | Threonine |
| Val | Valine |
| Trp | Tryptophan |
| Tyr | Tyrosine |

It will be appreciated that the novel compounds of the invention can be prepared and used in the free amine or free acid forms or as salts thereof. Amine salts can be, e.g., hydrochloride, trifluoracetate or tosylate salts and the like.

Carboxylic acid salts can be, e.g., sodium, potassium, calcium, ammonium, mono- di- or tri-substituted or quaternary ammonium salts and the like.

Preferred compounds of Formula II have amino acid moieties conveniently illustrated by the following groups:

Gly-OH,

Gly-OEt,

Gly-Ot-Bu,

NH(CH$_2$)$_2$CO$_2$Et,

Gly-Gly-OEt,

N-(Gly-OEt)-Gly-OEt,

N-(CH$_3$)-Gly-OEt,

N-(Ph)-Gly-OEt,

N-(Bn)-Gly-OEt, (±)-NHCH$_2$CH(CH$_3$)CO$_2$Et,

L-Ala-OEt,

L-NHCH$_2$CH(CH$_3$)CO$_2$Et,

D-Ala-OEt,

L-Ile-OEt,

D-Ile-OEt,

L-Phe-OH,

NHCH$_2$CH(CH$_2$Bn)CO$_2$Et,

L-Phe-OEt,

L-Phe-O-t-Bu,

D-Phe-OH,

D-Phe-O-Et,

D-Phe-O-t-Bu,

L-Glu(OBzl)-OEt,

D-Glu(OBzl)-OEt,

D-Lys(Cl-Z)-OEt,

L-Lys(Cl-Z)-OEt,

L-Trp-OEt,

D-Trp-OEt,

L-Thr(OBzl)-OEt, and

D-Thr(OBzl)-OEt.

In accordance with another embodiment of the invention, certain other illustrative compounds of Formula I can be represented by the following structural Formulas IIIa and IIIb:

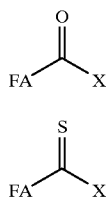
(IIIa)

(IIIb)

wherein:
FA is a heteroatom-containing fatty acid moiety selected from the group consisting of $CH_3O(CH_2)_{11}$— and $CH_3(CH_2)_9O(CH_2)_2$—;
X is selected from the group consisting of amido, monoalkyl-amido, dialkyl-amido, monoaryl-amido, monoaryl-amido substituted with OH or halogen, diaryl-amido, and diaryl-amido substituted with OH or halogen;
and in which the number of carbon atoms in alkyl are from one to eight and the number of carbon atoms in aryl is six.

In the above Formulas IIIa and IIIb, X is illustrated hereinbelow with the following groups:
$NH_2$,
NHBn,
$NEt_2$,
$NHCH_2CH_2Ph$,

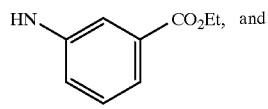

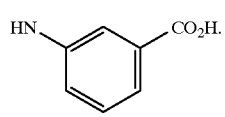

In still another embodiment of the invention, other illustrative compounds of Formula I can be represented by the following structural Formula IV:

FA-X      (IV)

wherein:

FA is a heteroatom-containing fatty acid moiety selected from the group consisting of $CH_3(CH_2)_{11}$— and
$CH_3(CH_2)_9O(CH_2)_2$—;

X is selected from the group consisting of cyano, tetrazole, N-alkyltetrazole and N-arylalkyltetrazole;
and in which the number of carbon atoms in alkyl is from one to eight, and the number of carbon atoms in aryl is six.

In the above Formula IV, X is illustrated herein below with the following groups:

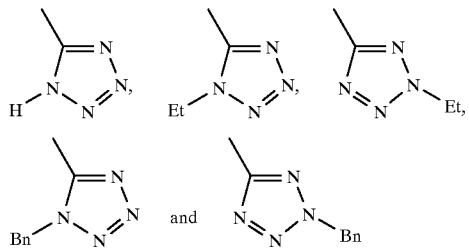

Other preferred compounds of the invention are conveniently represented by the following structural Formula V:

$CH_3O(CH_2)_7$—X—$(CH_2)_2$—Y      (V)

wherein X is $CH_2$ or O, and Y is $COCH_3$ or $CH_2OH$.

Still other preferred compounds of the invention are conveniently represented by the following structural Formula VI:

$CH_3(CH_2)_9O(CH_2)_2$—X      (VI)

wherein X is selected from the group consisting of
CN,
$CONEt_2$,
$CONHCH_2Ph$,
CO-Gly-OEt,
CO-D-Phe-OEt, and
CO-L-Phe-OEt.

Preferred compounds included within the scope of the foregoing structural formulas are the following:

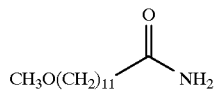

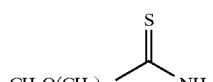

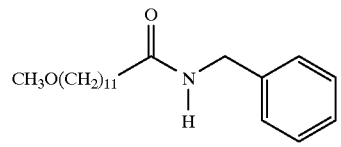

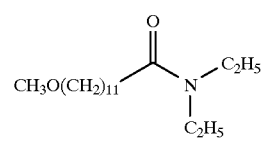

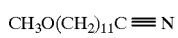
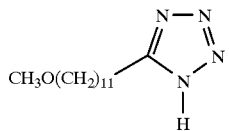
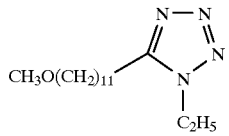
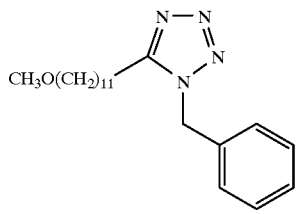
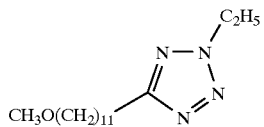
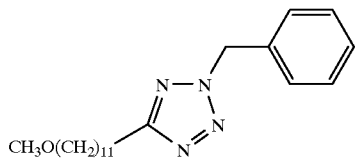
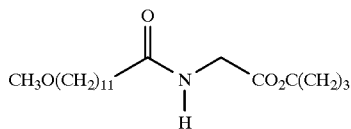
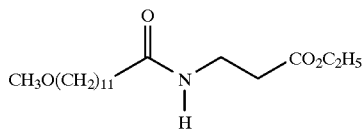
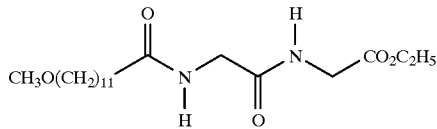
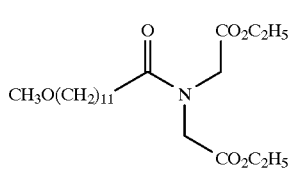
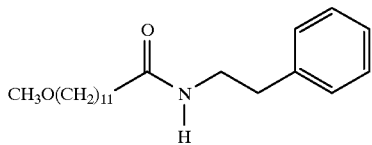
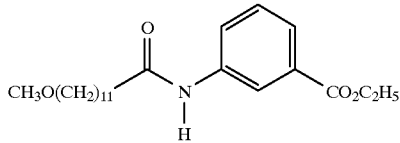
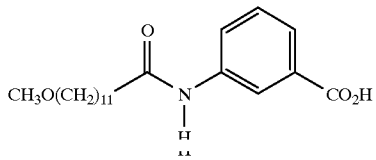
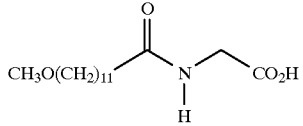
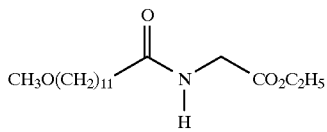
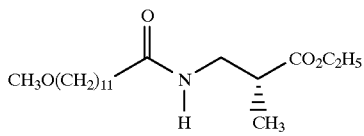
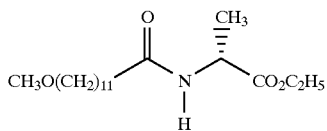
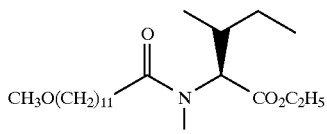
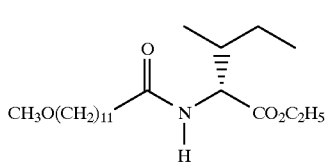

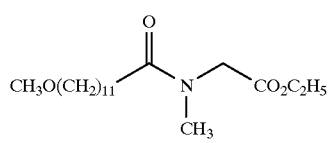
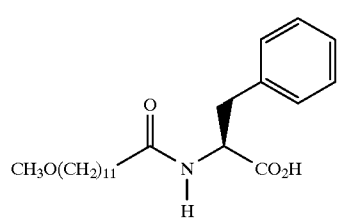
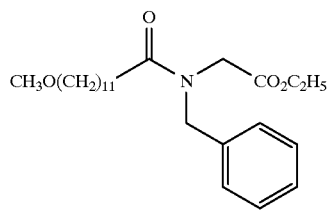
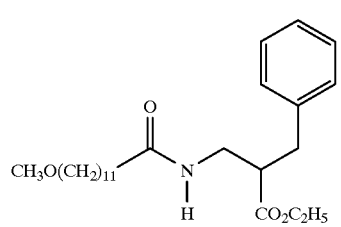
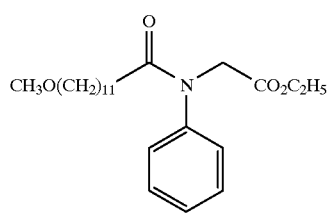
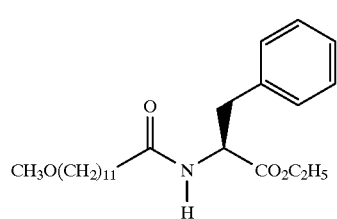
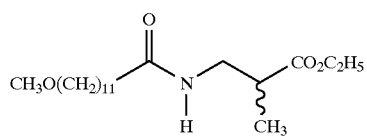
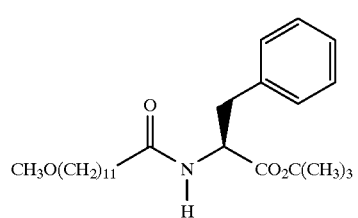
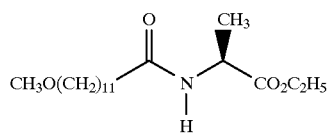
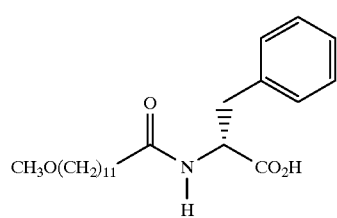
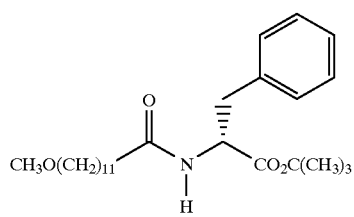
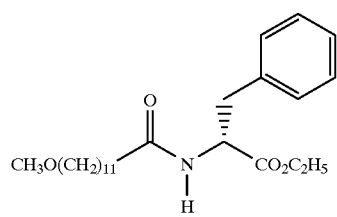
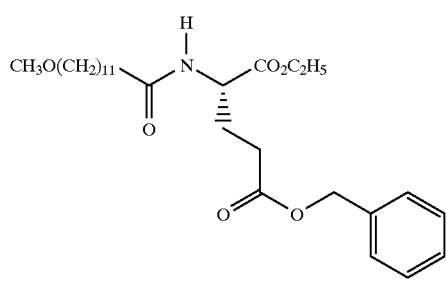
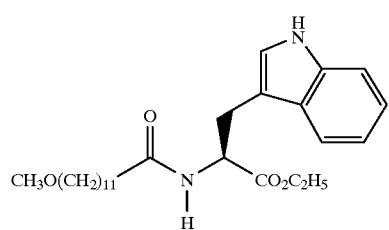

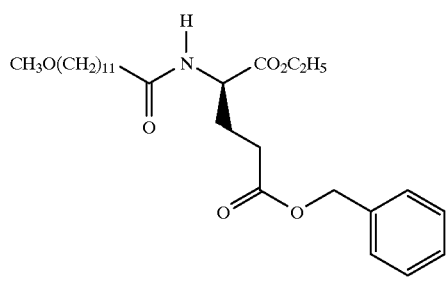
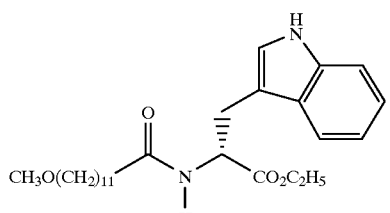
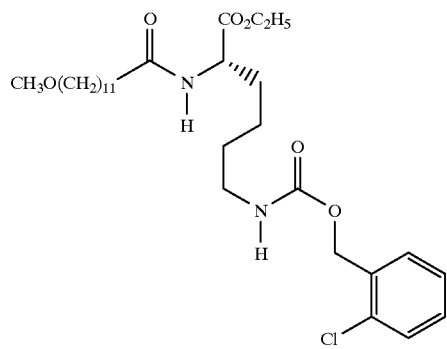
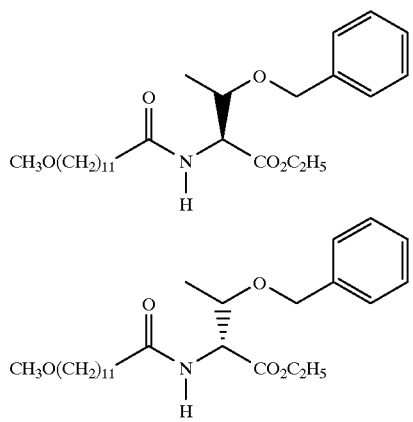
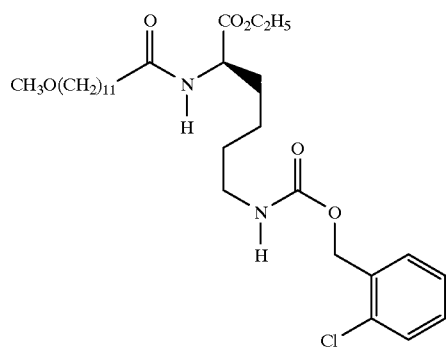
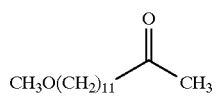
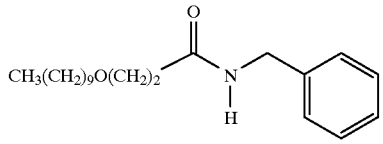
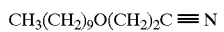
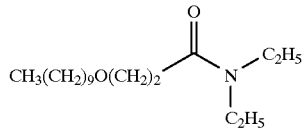
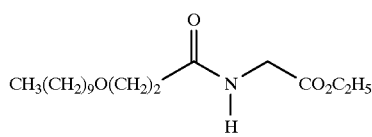
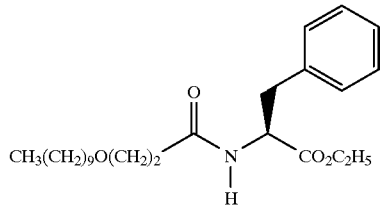
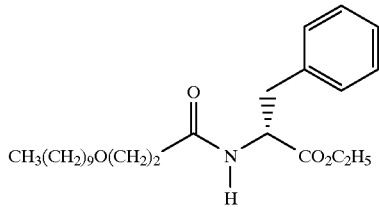
The novel compounds of this invention can be synthesized by various methods of preparation as illustrated by the following generic Reaction Schemes 1 to 18.

Scheme 1
Generic Preparation of Fatty Acids
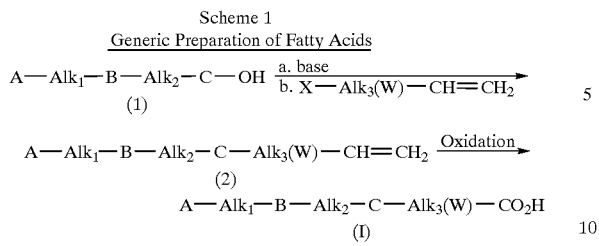
Scheme 2
Preparation of 4-[(7-Methoxyheptyl) oxy]butanoic Acid
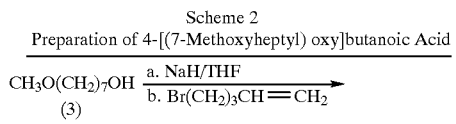
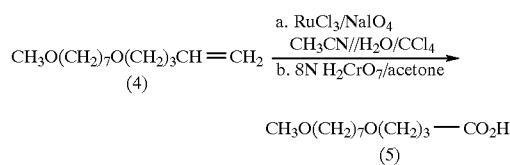
Scheme 3
Generic Preparation of Amide Analogs
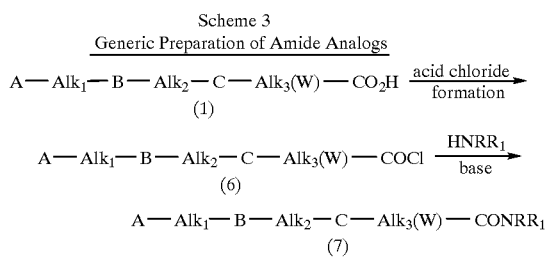
Scheme 4
Preparation of 12-Methoxy-N-(phenylmethyl)-dodecanamide
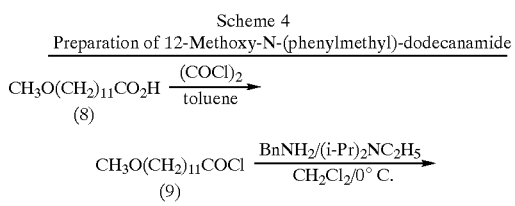
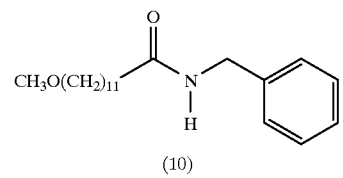
Scheme 5
Generic Preparation of Amino Acid Analogs
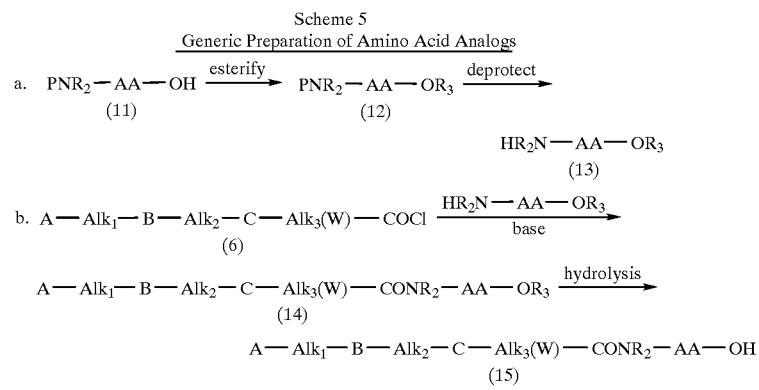
Scheme 6
Preparation of N-(12-Methoxy-1oxododecyl)-D-alanine Ethyl Ester
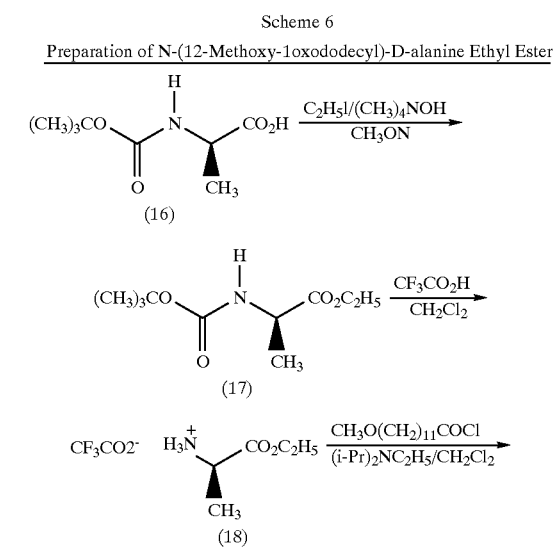
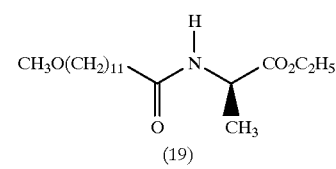

Scheme 7
Preparation of N-(12-Methoxy-1-oxododecyl)-glycine

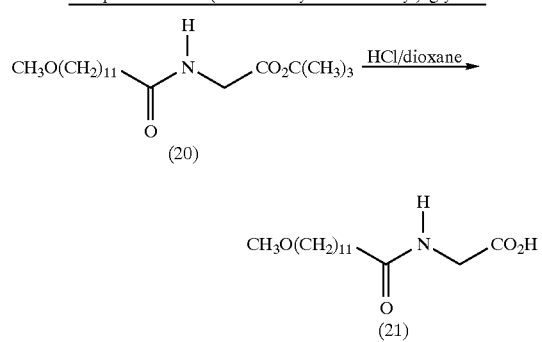

Scheme 8
Generic Preparation of Esters

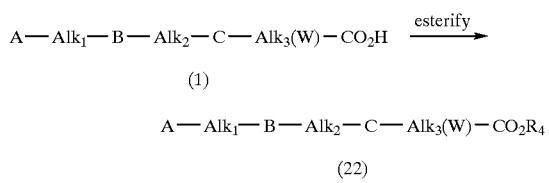

Scheme 9
Preparation of Ethyl 12-Methoxydodecanoate

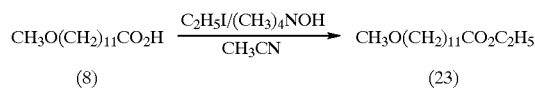

Scheme 10
Generic Preparation of Ketones

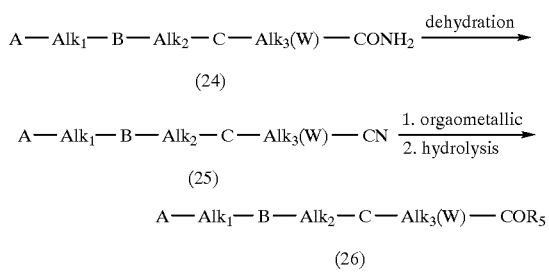

Scheme 11
Preparation of 13-Methoxy-2-tridecanone

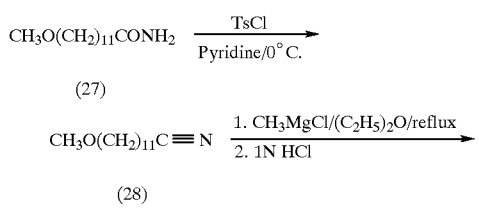

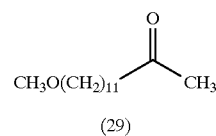

(29)

Scheme 12
Generic Preparation of Alcohols

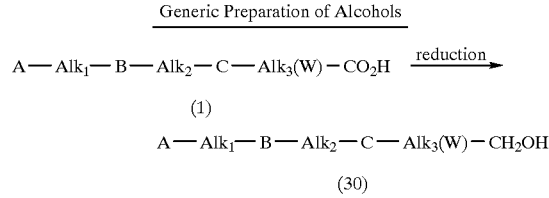

Scheme 13
Preparation of 12-Methoxydodecanol

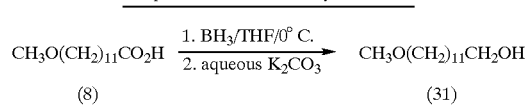

Scheme 14
Generic Preparation of Thioamides

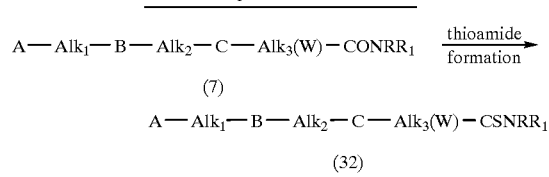

Scheme 15
Preparation of 12-Methoxydodecanethioamide

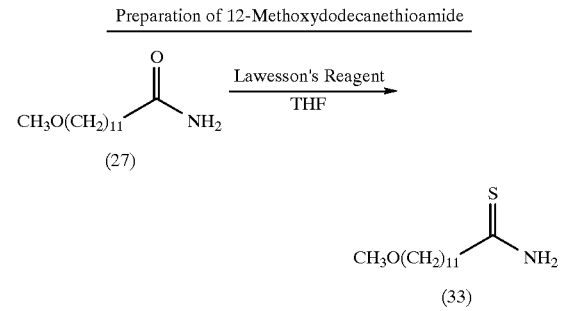

Scheme 16
Generic Preparation of Tetrazoles

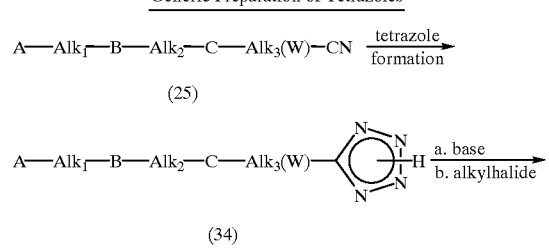

-continued

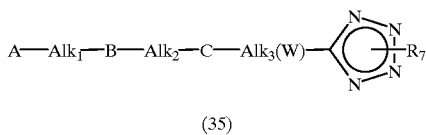

(35)

Scheme 17
Preparation of 5-(11-Methoxyundecyl)-1H-tetrazole

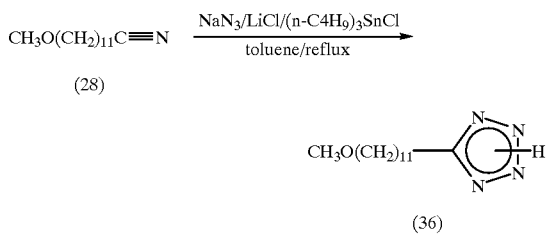

Scheme 18
Preparation of 1-Ethyl-5-(11-methyoxyundecyl)-1H-tetrazole
and 2-Ethyl-5-(11-methoxyundecyl)-2H-tetrazole

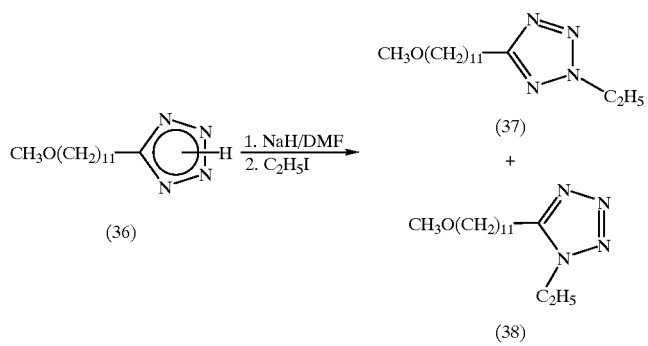

Reaction Scheme 1 illustrates the generic preparation of fatty acids of Formula I in which A, B, C, $Alk_1$, $Alk_2$, $Alk_3$ and W are defined as hereinbefore from the reaction of alcohols and ω-halo alkenes via a nucleophilic displacement followed by subsequent oxidative cleavage of the vinyl moiety.

Accordingly, alcohol (1) is treated with base (e.g. sodium hydride, n-butyllithium or potassium t-butoxide) in an organic solvent such as tetrahydrofuran (THF) or diethylether to form the alkoxide which is then coupled with an ω-halo alkene to form the chain extended alkene (2) which is then converted to the fatty acid (I) by oxidative cleavage of the alkene moiety using an oxidizing agent (e.g. $KMnO_4$, $H_2CrO_7$ or $RuCl_3/NaIO_4$) in a biphasic solvent system to give the fatty acid (I).

Reaction Scheme 2 illustratively shows the preparation of 4-[(7-methoxyheptyl)-oxy]butanoic acid wherein 7-methoxyheptan-1-ol(3) is treated with sodium hydride in tetrahydrofuran (THF) followed by the addition of 5-bromopentene to form 6,14-dioxapentadecan-1-ene(4) which in turn is treated with ruthenium(III) chloride hydrate ($RuCl_3 \cdot xH_2O$) and sodium periodate ($NaIO_4$) in a 1:1.5:1 mixture of acetonitrile, water and carbon tetrachloride to form a mixture of aldehyde and carboxylic acid which is subsequently treated with Jones Reagent ($H_2CrO_7$/acetone) to give the desired fatty acid (5).

Reaction Scheme 3 illustrates the generic preparation of fatty acid amide analogs of Formula 7 in which A, B, C, $Alk_1$, $Alk_2$, $Alk_3$, W, R and $R_1$ are defined as hereinbefore from carboxylic acids of Formula I by reacting the fatty acid analog with an inorganic acid halide (e.g. $PCl_5$, $PCl_3$, $SOCl_2$) or acyl halides [e.g. $(COCl)_2$] in an organic solvent such as methylene chloride or toluene to form the corresponding fatty acid chloride (6) followed by coupling with an appropriate primary or secondary organic amine (e.g. benzylamine, diethylamine, morpholine) in an organic solvent such as methylene chloride, tetrahydrofuran (THF), or acetonitrile to give the fatty acid amide analog (7).

Reaction Scheme 4 illustratively shows the preparation of 12-methoxy-N-(phenyl-methyl)dodecanamide wherein 12-methoxydodecanoic acid (8) is treated with oxalyl chloride in anhydrous toluene to form 12-methoxydodecanoyl chloride (9) which in turn reacts with benzylamine in methylene chloride to give the desired fatty acid amide (10).

Reaction Scheme 5 illustrates the generic preparation of fatty acid amino acid analogs of Formula 14 in which A, B, C, $Alk_1$, $Alk_2$, $Alk_3$, W, $R_2$, $R_3$ and AA are defined as hereinbefore from a protected amino acid (11) where P is a standard amine protecting group (e.g. tert-butyloxy or benzylcarboxy) well known to one skilled in the art (see T. W. Greene and P. G. N. Wuts, "Protective Groups in Organic Synthesis", John Wiley & Sons, 1991).

The compound of Formula 11 is converted by either (i) acid catalyzed esterification or (ii) SN2 alkylation of the corresponding carboxylate salt to form the corresponding amino acid ester (12) which is then subjected to deprotection of the amine protecting group by either (i) acid hydrolysis (e.g. trifluoroacetic acid or hydrochloric acid) in an organic solvent such as methylene chloride or dioxane or (ii) by catalytic hydrogenolysis to form the amine (13) as either the ammonium salt or the free base, respectively. Treatment of the amine or its ammonium salt (13) with a fatty acid chloride (8) in an organic solvent such as methylene chloride, tetrahydrofuran (THF) or acetonitrile gives the fatty acid amino acid ester analog (14) which is converted to the fatty acid amino acid analog (15) by acid or base catalyzed hydrolysis.

Reaction Scheme 6 illustratively shows the preparation of N-(12-methoxy-1-oxododecyl)-D-alanine, ethyl ester wherein N-(t-butyloxycarbonyl)-D-alanine (16) is treated with tetramethylammonium hydroxide pentahydrate in acetonitrile followed by the addition of ethyl iodide to form N-(t-butyloxycarbonyl)-D-alanine, ethyl ester (17) which in turn reacts with trifluoroacetic acid in methylene chloride to give the trifluoroacetate salt of D-alanine ethyl ester (18) which, when treated with 2-methoxydodecanoyl chloride (9) in methylene chloride, gives the desired fatty acid amino ester (19).

Reaction Scheme 7 illustrates the preparation of N-(12-methoxy-1-oxododecyl)-glycine (21) wherein N-(12-methoxy-1-oxododecyl)-glycine 1,1-dimethylethyl ester (20) is treated with hydrochloric acid in dioxane to give the desired fatty acid amino acid (21).

Reaction Scheme 8 illustrates the generic preparation of fatty acid esters of Formula 22 in which A, B, C, $Alk_1$, $Alk_2$, $Alk_3$, W and R4 are defined as hereinbefore by converting carboxylic acids of Formula I by either (i) acid catalyzed esterification or (ii) SN2 alkylation of the corresponding carboxylate salt to form the corresponding fatty acid ester (22).

Reaction Scheme 9 illustratively shows the preparation of ethyl 12-methoxydodecanoate wherein 12-methoxydodecanoic acid (8) is treated with tetramethylammonium hydroxide pentahydrate in acetonitrile followed by the addition of ethyl iodide to give the desired fatty acid ester (23).

Reaction Scheme 10 illustrates the generic preparation of ketones of Formula 26 in which A, Br C, $Alk_1$, $Alk_2$, $Alk_3$, W and $R_5$ are defined as hereinbefore by reacting the fatty acid amides of Formula 24 with dehydrating agents (e.g. $P_2O_5$, $SOCl_2$, $PCl_3$, $PCl_5$, TsCl) in an organic solvent such as toluene or pyridine to give the corresponding nitrile (25) followed by treatment with an organometallic reagent, e.g. a Grignard reagent, and subsequent hydrolysis of the intermediate ketimine salt to form the ketone (26).

Reaction Scheme 11 illustratively shows the preparation of 13-methoxy-2-tridecanone (29) wherein 12-methoxydodecanamide (27) is treated with p-toluenesulfonyl chloride in pyridine to give the nitrile (28) which is first treated with methylmagnesium chloride in diethylether followed by aqueous HCl to give the desired ketone (29).

Reaction Scheme 12 illustrates the generic preparation of alcohols of Formula 30 in which A, B, C, $Alk_1$, $Alk_2$, $Alk_3$, and W are defined as hereinbefore by treating the carboxylic acid (I) with a reducing agent (e.g. borane, lithium aluminum hydride) in an organic solvent such as diethylether, tetrahydrofuran (THF) or dioxane followed by hydrolysis under acidic or basic conditions to afford the alcohol (32).

Reaction Scheme 13 illustratively shows the preparation of ethyl 12-methoxy-dodecanoate wherein 12-methoxydodecanoic acid (8) is treated with borane in tetrahydrofuran followed by hydrolysis with aqueous potassium carbonate to give the desired alcohol (31).

Reaction Scheme 14 illustrates the generic preparation of thioamides of Formula 32 in which A, B, C, $Alk_1$, $Alk_2$, $Alk_3$, W, $R_1$ and R are defined as hereinbefore by subjecting the fatty acid amide of Formula 7 to a thionation reaction ($P_2S_5$, $S_8$, Lawesson's Reagent) in an organic solvent such as tetrahydrofuran (THF), methylene chloride or dioxane to form the thioamide (32).

Reaction Scheme 15 illustratively shows the preparation of 12-methoxydodecanethioamide (33) wherein 12-methoxydodecanamide (27) is treated with Lawesson's Reagent in tetrahydrofuran (THF) to give the desired thioamide (33).

Reaction Scheme 16 illustrates the generic preparation of alkylated tetrazoles of Formula 35 in which A, B, C, $Alk_1$, $Alk_2$, $Alk_3$, W, and $R_7$ are defined as hereinberfore by converting the fatty acid nitrile (25) into the tautomeric free tetrazole (34) using an azide reagent (e.g. $NH_4Cl/NaN_3$, $Me_3SnN_3$ or $Bu_3SnCl/NaN_3/LiCl$) which is then alkylated with a variety of electrophiles (e.g. ethyl iodide or benzyl bromide) to give the alkylated tetrazole (35).

Reaction Scheme 17 illustratively shows the preparation of 5-(11-methoxyundecyl)-1H-tetrazole (36) wherein 12-methoxydodecanenitrile (28) is treated with a mixture of sodium azide, tri-n-butyltin chloride and lithium chloride toluene to give the desired tetrazole (36).

Reaction Scheme 18 illustratively shows the preparation of both regioisomers of ethyl-5-(11-methoxyundecyl)-H-tetrazole (37 and 38) wherein 5-(11-methoxyundecyl)-1H-tetrazole (36) is treated with sodium hydride in dimethylformamide followed by the addition of ethyl iodide to give the desired alkylated tetrazoles (37 and 38).

The general methods outlined in the foregoing Reaction Schemes are readily adaptable to variations by persons skilled in the art. For example, it is well known that one electrophilic group can be substituted for another electrophilic group and one nucleophilic group can be substituted for another nucleophilic group.

More specifically, nucleophiles such as sulfhydryl, substituted amino or amino groups can be substituted for hydroxyl groups. Likewise, electrophiles such as halogens, sulfonate esters, trifluoroacetate esters and the like can be employed interchangeably. The order of connection of, for example, A, $Alk_1$, $Alk_2$, $Alk_3$ can be varied. Protecting groups can be employed if desired.

Examples of protecting groups are tert-butyl esters, isoxazoles, trifluoroacetates, tetrahydropyranyl ethers and the like as referred to in the Green and Wuts text cited hereinbefore.

Likewise, one skilled in the art can readily replace other components mentioned in the foregoing Reaction Schemes. For example, one can use non-protic or dipolar aprotic solvents such as xylene, dimethoxyethane, diethoxyethane, sulfolane, dimethylformamide, dimethylsulfoxide, dioxane, furan, thiophene, dimethyl-acetamide, heptane, tetramethylurea and the like. Alternative protic solvents include methanol, water, isopropanol, tert-butanol, ethoxyethanol and the like which may replace the exemplified protic solvents when the solvent is not also used as a specific reagent.

The preferred temperature for the reactions disclosed in the Reaction Schemes and Examples is room temperature unless otherwise specified; however, in some cases temperatures between −78° and solvent reflux may be used. Many Examples disclosed require a dry atmosphere to obtain the best results or for safety reasons. An inert atmosphere may also be used such as that obtained using an atmosphere of argon or nitrogen.

Alternative non-reagent amine bases for the disclosed Reaction Schemes include, for example, N-methylmorpholine, diazabicyclononane and N,N-dimethylaminopyridine (DMAP) and the like. Mineral bases can include sodium carbonate, sodium bicarbonate, potassium hydroxide, sodium hydroxide, lithium hydroxide, lithium carbonate, calcium carbonate, barium hydroxide and aluminum hydroxide or oxide.

Hydride bases can include lithium hydride, calcium hydride, potassium hydride and the like as well as organometallic bases such as tert-butyl lithium, lithium acetylide, ethyl magnesium bromide, isopropyl magnesium chloride and the like. Other useful acids can include, for example, hydrogen bromide (hydrobromic acid), sulfuric acid, phosphoric acid, potassium phosphate, toluene sulfonic acid, benzene sulfonic acid, methane sulfonic acid, benzyl phosphoric acid, trifluromethyl sulfonic acid, nitrobenzoic acid, trichloroacetic acid and acetic acid as well as Lewis acids such as aluminum chloride, borontrifluoride, tin chlorides, titanium halides and the like.

Hydrogenation catalysts for use in the above Reaction Schemes can include, for example, palladium chloride, palladium metal of various mesh sizes, palladium on barium sulfate, nickel, platinum and platinum oxide with hydrogen gas as well as with hydrogen transfer reagents such as cyclohexadiene and cyclohexene used with or without pressures greater than atmospheric pressure.

The sulfoxides of this invention are readily prepared by treating the appropriate sulfide with an oxidizing agent and the sulfones can be prepared either directly from the sulfide or from the sulfoxide. Suitable oxidizing agents include, but are not limited to, hydrogen peroxide, metal periodates, periodic acid, peracetic acid, meta-chloroperbenzoic acid, tert-butyl hypochlorite or optically active agents that induce optical activity in the product such as percamphoric acid. These oxidations can be carried out at temperatures ranging from −80° C. to solvent reflux but the preferred temperatures are between −20° and 35° C.

Although specific methods of production are described herein, it will be appreciated that the novel antiviral compounds claimed herein are not limited to any particular method of production.

In standard biological tests, the novel compounds of this invention have been shown to have inhibitory activity against the human immunodeficiency virus (HIV), which is a lentivirus.

Inhibitory activity against HIV-1 was shown by tests involving plating of susceptible human host cells which are syncytium-sensitive with and without virus in microculture plates, adding various concentrations of the test compound, incubating the plates for 7 to 9 days (during which time infected, non-drug treated control cells are largely or totally destroyed by the virus), and then determining the remaining number of viable cells with a colorometric endpoint.

The following Examples will further illustrate the invention in greater detail, although it will be understood that the invention is not limited to these specific Examples or the specific details described therein.

From these specific examples and the general disclosure hereinbefore, the person skilled in the art will readily appreciate and recognize numerous other examples within the scope of the appended claims without departing from the spirit and scope of the claims appended below.

EXAMPLE 1

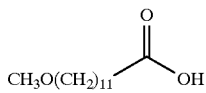

12-Methoxydodecanoic Acid

12-Bromoundecanoic acid (20 g, 72 mmol) in 600 mL of methanol was added dropwise to a solution of sodium methoxide in methanol (50 mL, 4.4 M) at 0° C. After stirring at room temperature for 2 hours, the resulting cloudy solution was refluxed for 46 hours. The solvent was removed by rotary evaporator and the residue partioned between diethyl ether and water. The aqueous phase was acidified to pH 1 with 6 N HCl and extracted with two portions of diethyl ether. The combined organic extracts were washed with brine, dried over magnesium sulfate, filtered and concentrated to give the title compound (16.1 g) as a white solid, m.p. 45.9–48.0° C. (DSC). The structure was supported by NMR, infrared spectroscopy, elemental analysis and mass spectroscopy.

Analysis for $C_{13}H_{26}O_3$ (MW 230.4): Calcd.: C, 67.79; H, 11.38. Found: C, 67.62; H, 11.53.

EXAMPLE 2

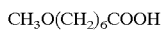

7-Methoxyheptanoic Acid

The title compound was prepared by the method of Example 1 using 7-bromoheptanoic acid (50 g, 239 mmol) instead of 12-bromoundecanoic acid and dimethylformamide (300 mL) instead of methanol as the solvent. Concentration afforded the title compound (30 g) as a pale yellow liquid and the structure verified by NMR.

EXAMPLE 3

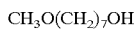

7-Methoxy-1-heptanol

To a solution of the title product of Example 2 (18.3 g, 114 mmol) in 60 mL of tetrahydrofuran at 0° C. was added dropwise a solution of borane in tetrahydrofuran (175 mL, 1M). After stirring at room temperature for 3 days, 300 mL of water was added followed by solid $K_2CO_3$ (31.7 g, 229 mmol). The layers were separated and the aqueous phase extracted with three portions of diethyl ether. The combined organic extracts were washed with brine, dried over magnesium sulfate, filtered and concentrated. The crude product was purified by distillation at reduced pressure (8 mm Hg) to give the title compound (12 g), b.p. 107–110° C. The structure was verified by NMR.

EXAMPLE 4

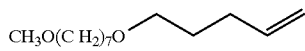

1-Methoxy-7-(4-pentenyloxy)heptane

Sodium hydride (665 mg, 17 mmol, washed three times with hexane) was treated with the title product of Example 3 (2.0 g, 14 mmol) in 90 mL of tetrahydrofuran at reflux for one hour. A solution of 5-bromopentene (2.0 g, 14 mmol) in 50 mL of tetrahydrofuran was added dropwise and refluxing continued for 20 hours. After cooling to room temperature, 50 mL of water was added, the layers separated and the aqueous phase was extracted with two portions of ethyl acetate. The combined organic extracts were washed with brine, dried over magnesium sulfate, filtered and concentrated. Chromatography of the crude residue on silica gel using 50-50 ethyl acetate-heptane as eluant gave the title compound (485 mg) as a yellow oil and the structure verified by NMR.

EXAMPLE 5

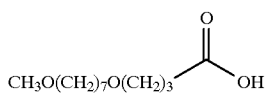

4-[(7-Methoxyheptyl)oxy]butanoic Acid

To a heterogeneous solution of the title product of Example 4 (319 mg, 1.5 mmol) in 3 mL of carbon tetrachloride, 3 mL of acetonitrile and 4.5 mL of water was added sodium metaperiodate (1.4 g, 6.4 mmol) followed by ruthenium trichloride hydrate (9 mg, 40 mmol). After stirring vigorously for 3 hours at room temperature, the mixture was diluted with methylene chloride, the layers separated and the aqueous phase extracted with two portions of methylene chloride. The combined organic extracts were washed with brine, dried over magnesium sulfate, filtered and concentrated affording a mixture of oxidized products. To this mixture in 5 mL of acetone was added Jones Reagent (8N $H_2CrO_7$) dropwise until the usual orange color persisted. The reaction was partioned between diethyl ether and water, the layers separated and the aqueous phase extracted with two portions of diethyl ether. The combined organic extracts were washed with brine, dried over magnesium sulfate, filtered and concentrated. Chromatography of the crude residue on silica gel using 30-70 ethyl acetate-hexane as eluant gave the title compound (217 mg) as a yellow oil. The structure was supported by NMR, infrared spectroscopy, elemental analysis and mass spectroscopy.

Analysis for $C_{12}H_{24}O_4$ (MW 232.3): Calcd.: C, 62.04; H, 10.41. Found: C, 61.79; H, 10.73.

EXAMPLE 6

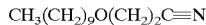

3-(Decyloxy)propanenitrile

Sodium hydride (200 mg, 5 mmol; washed three times with hexane) was treated with 1-decanol (12 mL, 63 mmol) for 1 hour at room temperature. Acrylonitrile (10 mL, 152 mmol) was added dropwise and the resulting paste warmed to 60° C. for 2 hours. After cooling to room temperature, the paste was dissolved in diethyl ether and washed with copious water, one portion of brine, dried over magnesium sulfate, filtered and concentrated. Chromatography of the crude residue on silica gel using 25-75 ethyl acetate-hexane as eluant gave the title compound (5.5 g) as a water-white liquid. The structure was supported by NMR, infrared spectroscopy, elemental analysis and mass spectroscopy.

Analysis for $C_{13}H_{25}NO$ (MW 211.4): Calcd.: C, 73.88; H, 11.92; N, 6.63. Found: C, 74.00; H, 11.84; N, 6.49.

EXAMPLE 7

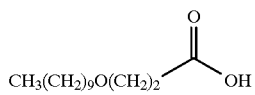

3-(Decyloxy)propanoic Acid

To a suspension of the title product of Example 6 (3.8 g, 18 mmol) in 140 mL of concentrated HCl was added 25 mL of glacial HOAc and the resulting mixture refluxed for 20 hours. After cooling to room temperature, the solvent was removed by rotary evaporator and the resulting residue partioned between ethyl acetate and water. The aqueous phase was extracted with two portions of ethyl acetate, the combined organic phases washed with brine, dried over magnesium sulfate, filtered and concentrated. The crude product was dissolved in diethyl ether and washed with two portions of saturated $NaHCO_3$ and one portion of water. The basic washes were combined and acidified to pH 3 with 1 N HCl. The resulting solid was filtered, washed with copious water and air dried for 3 hours to give the title compound (1.9 g) as a white solid, m.p. 41.5–43.9° C. (DSC). The structure was supported by NMR, infrared spectroscopy, elemental analysis and mass spectroscopy.

Analysis for $C_{13}H_{26}O_3 \cdot 0.15 H2O$ (MW 230.4): Calcd.: C, 67.00; H, 11.37. Found: C, 66.97; H, 11.18.

EXAMPLE 8

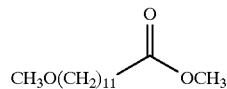

Methyl 12-Methoxydodecanoate

Tetramethylammonium hydroxide pentahydrate (1.7 g, 9.4 mmol) was added to a solution of the title product of Example 1 (2.0 g, 8.7 mmol) in 45 mL of anhydrous acetonitrile. After stirring for 4 hours at room temperature, methyl iodide (0.6 mL, 9.6 mmol) was added and the resulting milky solution stirred at room temperature. The solvent was removed by rotary evaporator and partioned between diethyl ether and water. The organic phase was washed with brine, dried over magnesium sulfate, filtered and concentrated to give the title compound (2.1 g) as a pale yellow liquid. The structure was supported by NMR, infrared spectroscopy, elemental analysis and mass spectroscopy.

Analysis for $C_{14}H_{28}O_3$ (MW 244.4): Calcd.: C, 68.81; H, 11.55. Found: C, 68.83; H, 11.65.

EXAMPLE 9

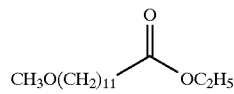

Ethyl 12-Methoxydodecanoate

The title compound was prepared by the method of Example 8 using ethyl iodide (0.8 mL, 10 mmol) instead of methyl iodide. Concentration afforded the title compound (2.2 g) as a pale yellow oil. The structure was supported by NMR, infrared spectroscopy, elemental analysis, and mass spectroscopy.

Analysis for $C_{15}H_{30}O_3$ (MW 258.4): Calcd.: C, 69.72; H, 11.70. Found: C, 69.74; H. 12.01.

EXAMPLE 10

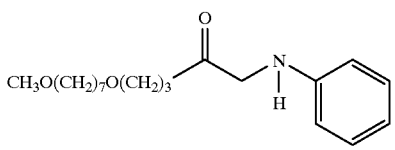

4-[(7-Methoxyheptyl)oxy]-N-(phenylmethyl)butamide

Oxalyl chloride is added dropwise to a solution of the title product of Example 5 in anhydrous toluene. After stirring at room temperature, the solvent is removed on a rotary evaporator, the residue is dissolved in anhydrous toluene and concentrated giving 4-[(7-methoxyheptyl)oxy]butanoyl chloride. To a solution of excess benzylamine in methylene chloride at 0° C. is added dropwise 4-[(7-methoxyheptyl)oxy]-butanoyl chloride. After stirring at room temperature, the reaction mixture is washed successively with 1N HCl, water, saturated NaHCO$_3$, water and brine, and is dried over magnesium sulfate, filtered and concentrated, thereby giving the title compound. The title compound is structurally analogous to the N-(phenylmethyl)alkylamide compounds prepared in Examples 14 and 20, hereinafter, and can be used in place thereof with substantially similar antiviral results.

EXAMPLE 11

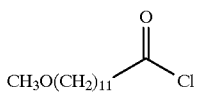

12-Methoxy-1-dodecanoyl Chloride

Oxalyl chloride (16.0 g, 70 mmol) was added dropwise to a solution of 12-methoxydodecanoic acid (9.8 g, 77 mmol) in 300 mL of anhydrous toluene. After stirring at room temperature for 16 hours the solvent was removed on a rotary evaporator. The residue was taken up in anhydrous toluene and concentrated to give the title compound (17.4 g) as a yellow liquid. The structure was verified by infrared spectroscopy (1796 cm$^{-1}$) and NMR.

EXAMPLE 12

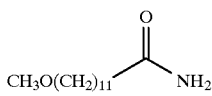

12-Methoxydodecanamide

To the title product from Example 11 (1.1 g, 4.3 mmol) in 70 mL of anhydrous tetrahydrofuran was added 20 mL of freshly distilled liquid ammonia in a Parr shaker which was sealed and shaken at room temperature for 16 hours. After filtering and concentration, the crude residue was dissolved in anhydrous methanol and passed through a basic ion exchange resin and eluted with anhydrous methanol. Concentration afforded the title compound (780 mg) as a white solid, m.p. 83.9–85.6° C. (DSC). The structure was supported by NMR, infrared spectroscopy, elemental analysis, and mass spectroscopy.

Analysis for C$_{13}$H$_{27}$NO$_2$ (MW 229.4): Calcd.: C, 68.08; H, 11.86; N, 6.11. Found: C, 68.40; HI 12.20; N. 5.84.

EXAMPLE 13

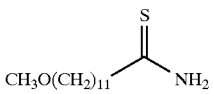

12-Methoxydodecanethioamide

To the title product from Example 12 (1.0 g, 5 mmol) in 70 mL of anhydrous tetrahydrofuran was added 2,4-bis(4-methoxyphenyl)-1,3-dithia-2,4-diphosphetane-2,4-disulfide [Lawesson's Reagent] (1.0 g, 2 mmol). After stirring at room temperature for 1 day, the solvent was removed by rotary evaporator and the resulting residue was purified by chromatography on silica gel using 30-70 ethyl acetate-hexane as eluant to give the title compound (625 mg) as a white solid, m.p. 86.8–89.2° C. (DSC). The structure was supported by NMR, infrared spectroscopy, elemental analysis, and mass spectroscopy.

Analysis for C$_{13}$H$_{27}$NOS (MW 245.4): Calcd.: C, 63.62; H, 11.09; N, 5.71; SI 13.06. Found: C, 63.59; H, 11.23; N, 5.50; S, 13.03.

EXAMPLE 14

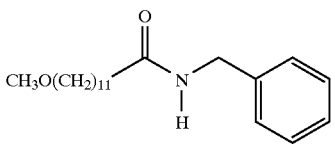

12-Methoxy-N-(phenylmethyl)dodecanamide

To a solution of benzylamine (486 mg, 4.5 mmol) in 20 mL of methylene chloride at 0° C. was added dropwise diisopropylethylamine (0.45 ml, 5 mmol) followed by the title product of example 11 (1.0 g, 4 mmol). After stirring at room temperature for 6 days, the reaction mixture was washed successively with 1N HCl, water, saturated NaHCO$_3$, water and brine, dried over magnesium sulfate, filtered and concentrated. The residue was dissolved in anhydrous methanol and passed through a basic ion exchange resin and eluted with anhydrous methanol. Concentration afforded the title compound (895 mg) as a white solid, m.p. 77.7–79.4° C. (DSC). The structure was supported by NMR, infrared spectroscopy, elemental analysis, and mass spectroscopy.

Analysis for C$_{20}$H$_{33}$NO$_2$ (MW 319.5): Calcd.: C, 75.19; H, 10.41; N, 4.38. Found: C, 74.87; H, 10.50; N, 4.32.

EXAMPLE 15

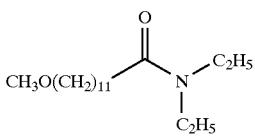

N,N-Diethyl-12-methoxydodecanamide

The title compound was prepared by the method of Example 14 using diethylamine (331 mg, 4.5 mmol) instead of benzylamine. The residue was dissolved in anhydrous methanol and passed through a basic ion exchange resin and eluted with anhydrous methanol. Concentration afforded the title compound (826 mg) as a pale yellow liquid. The structure was supported by NMR, infrared spectroscopy, elemental analysis, and mass spectroscopy.

Analysis for $C_{20}H_{33}NO_2$ (MW 319.5): Calcd.: C, 75.19; H, 10.41; N, 4.38. Found: C, 74.87; H, 10.50; N, 4.32.

EXAMPLE 16

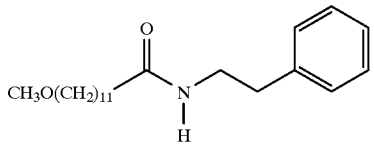

12Methoxy-N-(2-phenylethyl)dodecanamide

The title compound was prepared by the method of Example 14 using 2-phenylethylamine (534 mg, 4.4 mmol) instead of benzylamine. Chromatography of the crude residue on silica gel using 25-75 ethyl acetate-hexane as eluant gave the title compound (274 mg) as a white powder, m.p. 70.0–72.5° C. (DSC). The structure was supported by NMR, infrared spectroscopy, elemental analysis, and mass spectroscopy.

Analysis for $C_{21}H_{35}NO_2$ (MW 333.5): Calcd.: C, 75.63; Hp 10.58; N, 4.20. Found: C, 75,58; H, 10.72; N. 4.13.

EXAMPLE 17

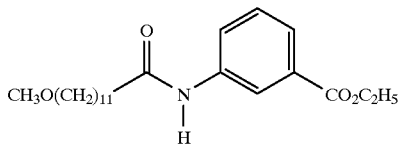

Ethyl 3-[(12-Methoxy-1-oxododecyl)amino]-benzoate

The title compound was prepared by the method of Example 14 using ethyl 3-aminobenzoate (1.4 g, 8.8 mmol) instead of benzylamine. Chromatography of the crude residue on silica gel using 25-75 ethyl acetate-hexane as eluant gave the title compound (1.5 g) as a white powder, m.p. 78.5–81.5° C. (DSC). The structure was supported by NMR, infrared spectroscopy, elemental analysis, and mass spectroscopy.

Analysis for $C_{22}H_{35}NO_4$ (MW 377.5): Calcd.: C, 69.99; H, 9.34; N, 3.71 Found: C, 70.00; H, 9.40; N, 3.67.

EXAMPLE 18

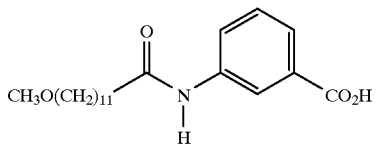

3-[(12-Methoxy-1-oxododecyl)amino]benzoic acid

To a solution of the title product of Example 17 (1.2 g, 3.1 mmol) in 60 mL of absolute ethanol was added dropwise an aqueous solution of lithium hydroxide (7 mL, 2M). After stirring at room temperature for 16 hours, the solvent was removed by rotary evaporator and the resulting residue partioned between diethyl ether and water. The organic phase was washed with brine and the aqueous washes combined. The pH of the combined aqueous washes was adjusted to 2 with 0.5N $KHSO_4$ and extracted with diethyl ether followed by methylene chloride. The organic extracts were combined and concentrated. The crude product was suspended in saturated $NaHCO_3$, filtered to remove insoluble materials and acidified with 6N HCl. The resulting solid was filtered, washed with copious water and air dried for 5 hours to give the title compound (371 mg) as a white solid, m.p. 168.6–171.4° C. (DSC). The structure was supported by NMR, infrared spectroscopy, elemental analysis, and mass spectroscopy.

Analysis for $C_{20}H_{31}NO_4$ 0.4 H2O (MW 349.5): Calcd.: C, 67.35; H, 8.99; N, 3.93 Found: C, 67.19; H, 8.95; N, 3.77.

EXAMPLE 19

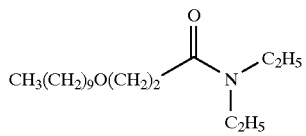

3-(Decyloxyl-N,N-diethylpropanamide

To a solution of diethylamine (0.1 mL, 0.97 mmol) in 4.4 mL of methylene chloride was added dropwise diisopropylethylamine (0.2 mL, 1.2 mmol), the title product of Example 7 (205 mg, 0.89 mmol) and 1-(3-dimethylaminopropyl)-3-ethylcarbodiimide hydrochloride (200 mg, 1.0 mmol). After stirring at room temperature, the reaction was diluted with methylene chloride and washed successively with water, 1N HCl, water, saturated aqueous $NaHCO_3$, water and brine, dried over magnesium sulfate and concentrated. Chromatography of the crude residue on silica gel using 30-70 ethyl acetate-heptane as eluant gave the title compound (96 mg) as a yellow liquid. The structure was supported by NMR, infrared spectroscopy, elemental analysis, and mass spectroscopy.

Analysis for $C_{17}H_{35}NO_2$ (MW 285.5): Calcd.: C, 71.53; H, 12.36; N, 4.91. Found: C, 71.76; H, 12.78; N, 4.81.

EXAMPLE 20

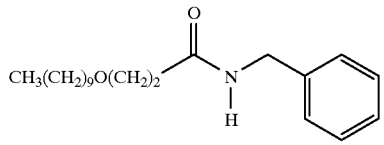

3-(Decyloxy-N-(phenylmethyl)propanamide

The title compound was prepared by the method of Example 19 using benzylamine (103 mg, 0.96 mmol) instead of diethylamine. Radial chromatography of the crude residue on silica gel using 20-80 ethyl acetate-heptane as eluant gave the title compound (39 mg) as a white solid, m.p. 65.2–67.7° C. (DSC). The structure was supported by NMR, infrared spectroscopy, elemental analysis, and mass spectroscopy.

Analysis for $C_{20}H_{33}NO_2$ (MW 319.5): Calcd.: C, 75.19; H, 10.41; N, 4.38. Found: C, 75.14; H, 10.42; N, 4.27.

EXAMPLE 21

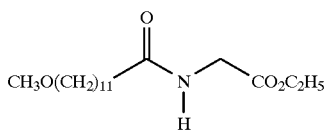

N-(12-Methoxy-1-oxododecyl)-glycine, Ethyl ester

The title compound was prepared by the method of Example 14 using glycine ethyl ester hydrochloride (1.2 g, 9.0 mmol) instead of benzylamine and triethylamine (2.4 mL, 17 mmol) instead of diisopropylethylamine. Concentration afforded the title compound (2.4 g) as a white solid, m.p. 73.9–76.7° C. (DSC). The structure was supported by NMR, infrared spectroscopy, elemental analysis and mass spectroscopy.

Analysis for $C_{17}H_{33}NO_4$ (MW 315.4): Calcd.: C, 64.73; H, 10.54; N, 4.44. Found: C, 64.51; H, 10.74; N, 4.43.

EXAMPLE 22

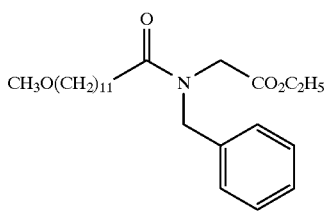

N-(12-Methoxy-1-oxododecyl)-N-(phenylmethyl)-glycine, Ethyl ester

The title compound was prepared by the method of Example 14 using N-glycine ethyl ester (0.82 mL, 4.4 mmol) instead of benzylamine. Chromatography of the crude residue on silica gel using 20-80 ethyl acetate-hexane as eluant gave the title compound (1.1 g) as a pale yellow oil. The structure was supported by NMR, infrared spectroscopy, elemental analysis, and mass spectroscopy.

Analysis for $C_{24}H_{39}NO_4$ (KW 405.6): Calcd.: C, 71.08; H, 9.69; N, 3.45. Found: C, 71.15; HI 9.90; N, 3.44.

EXAMPLE 23

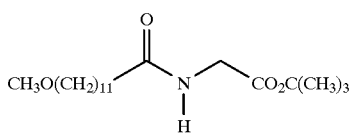

N-(12-Methoxy-1-oxodecyl)-glycine, 1,1-Dimethylethyl ester

The title compound was prepared by the method of Example 14 using glycine 1,1-dimethylethyl ester hydrochloride (2.0 g, 12 mmol) instead of benzylamine. Chromatography of the crude residue on silica gel using 25-75 ethyl acetate-hexane as eluant gave the title compound (2.3 g) as a white powder, m.p. 38.7–40.0° C. (DSC). The structure was supported by NMR, infrared spectroscopy, elemental analysis, and mass spectroscopy.

Analysis for $C_{19}H_{37}NO_4$ (MW 343.5): Calcd.: C, 66.44; H, 10.86; N, 4.08. Found: C, 66.38; H, 11.10; N, 4.03.

EXAMPLE 24

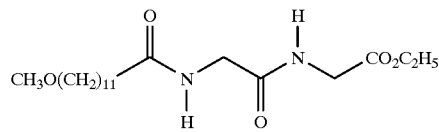

N-[N-(12-Methoxy-1-oxododecyl)glycyl]glycine, Ethyl ester

The title compound was prepared by the method of Example 14 using glycylglycine ethyl ester hydrochloride salt (356 mg, 2.2 mmol) instead of benzylamine. Chromatography of the crude residue on silica gel using 5-95-0.5 methanol-methylene chloride-ammonium hydroxide as eluant gave the title compound (500 mg) as a white powder, m.p. 117.9–121.3° C. (DSC). The structure was supported by NMR, infrared spectroscopy, elemental analysis, and mass spectroscopy.

Analysis for $C_{19}H_{36}N_2O_5$ (MW 372.5): Calcd.: C, 61.26; H, 9.74; N, 7.52. Found: C, 61.49; H, 9.75; N, 7.40.

EXAMPLE 25

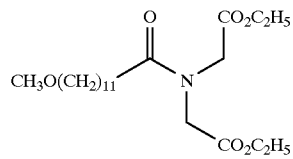

N-(2-Ethoxy-2-oxoethyl)-N-(12-methoxy-1-oxododecyl)glycine, Ethyl ester

The title compound was prepared by the method of Example 14 using N-(2-ethoxy-2-oxoethyl)glycine ethyl ester (420 mg, 2.2 mmol) instead of benzylamine. Chromatography of the crude residue on silica gel using 50-50 ethyl acetate-heptane as eluant gave the title compound (694 mg) as a water-white liquid. The structure was supported by NMR, infrared spectroscopy, elemental analysis, and mass spectroscopy.

Analysis for $C_{21}H_{39}NO_6$ (MW 401.5): Calcd.: C, 62.82; H, 9.79; N, 3.49. Found: C, 62.82; H, 9.97; N, 3.43.

EXAMPLE 26

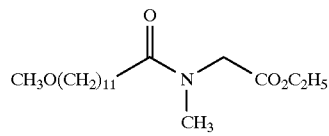

N-(12-Methoxy-1-oxododecyl)-N-methylglycine, Ethyl ester

The title compound was prepared by the method of Example 14 using N-methylglycine ethyl ester hydrochloride (339 mg, 2.2 mmol) instead of benzylamine. Chromatography of the crude residue on silica gel using 50-50 ethyl acetate-heptane as eluant gave the title compound (580 mg) as a white powder, m.p. 44.1–47.3° C. (DSC). The structure was supported by NMR, infrared spectroscopy, elemental analysis, and mass spectroscopy.

Analysis for $C_{18}H_{35}NO_4$ (MW 329.5): Calcd.: C, 65.62; H, 10.71; N, 4.25. Found: C, 65.84; H. 10.67; N, 4.21.

EXAMPLE 27

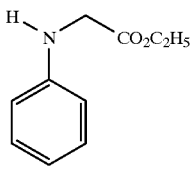

N-phenylglycine, Ethyl ester

To a solution of aniline (9.7 g, 104 mmol) and ethyl bromoacetate (16.3 g, 98 mmol) in 150 mL of absolute ethanol was added solid sodium acetate (8.1 g, 99 mmol) in portions. After stirring at room temperature, the solvent was removed by rotary evaporator and the residue suspended in diethyl ether, filtered through Celite and concentrated. Chromatography of the crude residue on silica gel using 20-80 ethyl acetate-hexane as eluant gave the title compound (580 mg) as a light brown solid. The structure was supported by NMR, infrared spectroscopy, elemental analysis, and mass spectroscopy.

Analysis for $C_{10}H_{13}NO_2$ (MW 179.2): Calcd.: C, 67.02; H, 7.31; N, 7.82. Found: C, 66.91; H, 7.41; No 7.79.

EXAMPLE 28

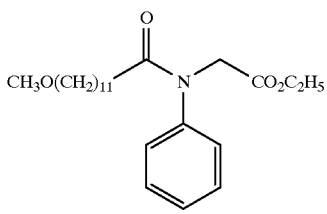

N-(12-Methoxy-1-oxododecyl)-N-phenylglycine, Ethyl ester

The title compound was prepared by the method of Example 14 using the product of Example 27 (397 mg, 2.2 mmol) instead of benzylamine. Chromatography of the crude residue on silica gel using 25-75 ethyl acetate-hexane as eluant gave the title compound (673 mg) as a beige powder, m.p. 56.8–59.3° C. (DSC). The structure was supported by NMR, infrared spectroscopy, elemental analysis, and mass spectroscopy.

Analysis for $C_{23}H_{37}NO_4$ (MW 391.6): Calcd.: C, 70.55; H, 9.52; N, 3.58. Found: C, 70.38; H, 9.28; N, 3.57.

EXAMPLE 29

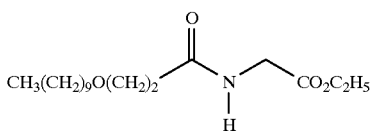

N-[3-(Decyloxy)-1-oxopropyl]glycine, Ethyl ester

The title compound was prepared by the method of Example 19 using glycine ethyl ester hydrochloride (131 mg, 0.94 mmol) instead of diethylamine. Chromatography of the crude residue on silica gel using 50-50-0.5 ethyl acetate-heptane-ammonium hydroxide as eluant gave the title compound (185 mg) as a white solid, m.p. 55.0–56.5° C. (DSC). The structure was supported by NMR, infrared spectroscopy, elemental analysis, and mass spectroscopy.

Analysis for $C_{17}H_{33}NO_4$ (MW 315.4): Calcd.: C, 64.73; H, 10.54; N, 4.44. Found: C, 64.75; H, 10.61; N, 4.38.

EXAMPLE 30

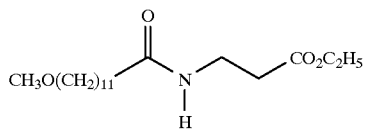

N-(12-Methoxy-1-oxododecyl)-β-alanine, Ethyl ester

The title compound was prepared by the method of Example 14 using β-alanine ethyl ester hydrochloride (248 mg, 1.6 mmol) instead of benzylamine. Chromatography of the crude residue on silica gel using 75-25 ethyl acetate-heptane as eluant gave the title compound (330 mg) as a white solid, m.p. 58.4–60.3° C. (DSC). The structure was supported by NMR, infrared spectroscopy, elemental analysis, and mass spectroscopy.

Analysis for $C_{18}H_{35}NO_4$ (MW 329.5): Calcd.: C, 65.62; H, 10.71; N, 4.25. Found: C, 65.64; H, 10.90; N, 4.22.

EXAMPLE 31

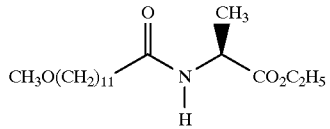

N-(12-Methoxy-1-oxododecyl)-L-alanine, Ethyl ester

The title compound was prepared by the method of Example 14 using L-alanine ethyl ester hydrochloride (690 mg, 4.5 mmol) instead of benzylamine. Chromatography of the crude residue on silica gel using 30-70 ethyl acetate-heptane as eluant gave the title compound (310 mg) as a white powder, m.p. 54.4–56.5° C. (DSC). The structure was supported by NMR, infrared spectroscopy, optical rotation ($[\alpha]_{365}^{25}$+24.4°, $CHCl_3$), elemental analysis, and mass spectroscopy.

Analysis for $C_{18}H_{35}NO_4$ (MW 329.5): Calcd.: C, 65.62; H, 10.71; N, 4.25. Found: C, 65.84; H, 10.74; N, 4.13.

EXAMPLE 32

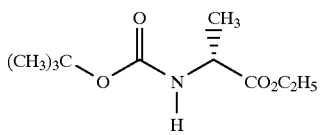

N-(t-Butyloxycarbonyl)-D-alanine, Ethyl ester

The title compound was prepared by the method of Example 8 using ethyl iodide (2.4 mL, 30 mmol) instead of methyl iodide and BOC-D-Ala-OH (5.0 g, 26.4 mmol) instead of the product of Example 1. Concentration afforded the title compound (2.8 g) as a pale yellow oil and the structure verified by NMR.

EXAMPLE 33

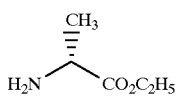

D-Alanine Ethyl ester Trifluoroacetate

The title product of Example 32 (2.8 g, 13 mmol) was dissolved in 50% aqueous trifluoroacetic acid and stirred at room temperature and the solvent removed by rotary evaporator after 1 hour. The residue was taken up with anhydrous toluene and the resulting paste was taken up in absolute ethanol and concentrated to give the trifluoroacetate salt of the title compound (3.2 g) as a brown viscous liquid and the structure verified by NMR.

EXAMPLE 34

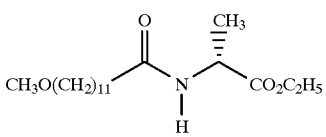

N-(12-Methoxy-1-oxododecyl)-D-alanine, Ethyl ester

The title compound was prepared by the method of Example 14 using the title product of Example 33 (2.8g, 12 mmol) instead of benzylamine and triethylamine (3.4 mL, 24 mmol) instead of diisopropylethylamine. Chromatography of the crude residue on silica gel using 25-75 ethyl acetate-hexane as eluant followed by a second chromatography on silica gel using 40-60 ethyl acetate-hexane as eluant gave the title compound (1.6 g) as a white powder, m.p. 53.5–56.1° C. (DSC). The structure was supported by NMR, infrared spectroscopy, optical rotation ($[\alpha]_{365}^{25}$–22.6°, CHCl$_3$), elemental analysis, and mass spectroscopy.

Analysis for C$_{18}$H$_{35}$NO$_4$ (MW 329.5): Calcd.: C, 65.62; H, 10.71; N, 4.25. Found: C, 66.01; H, 10.64; N, 4.22.

EXAMPLE 35

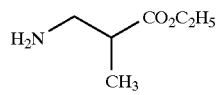

Ethyl 3-amino-2-methylpropanonate Hydrochloride

To a suspension of 3-aminoisobutyric acid (5.0 g, 48 mmol) in 180 mL of anhydrous ethanol was added acetylchloride (8.0 mL, 112 mmol) all at once and the resulting homogeneous solution reluxed for 24 hours. After cooling to room temperature, the solvent was removed by rotary evaporator, the residue was taken up in absolute ethanol and concentrated to give the hydrochloride salt of title compound (8.7 g) as a yellow liquid and the structure verified by NMR.

EXAMPLE 36

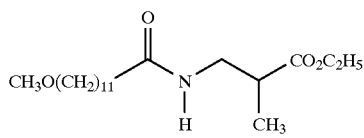

Ethyl 2-[[(12-methoxy-1-oxododecyl)amino]-2-methyl]propanoate

The title compound was prepared by the method of Example 14 using the title product of Example 35 (497 mg, 3 mmol) instead of benzylamine. Chromatography of the crude residue on silica gel using 50-50-0.5 ethyl acetate-heptane-ammonium hydroxide as eluant gave the title compound (889 mg) as a white powder, m.p. 53.1–56.2° C. (DSC). The structure was supported by NMR, infrared spectroscopy, elemental analysis, and mass spectroscopy.

Analysis for C$_{19}$H$_{37}$NO$_4$ (MW 343.5): Calcd.: C, 66.44; H, 10.86; N, 4.08. Found: C, 66.12; H, 10.57; N, 4.12.

EXAMPLE 37

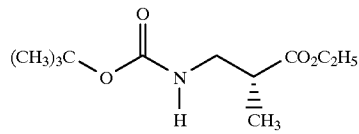

Ethyl N-(t-Butyloxycarbonyl-3-amino-2R-methylpropanoate

The title compound was prepared by the method of Example 8 using ethyl iodide (0.5 mL, 6 mmol) instead of methyl iodide and BOC-3-amino-2S-methyl-propanoic acid (1.0 g, 5 mmol; European Patent Appln. 327,523, published Nov. 7, 1990, Example 4) instead of the title product of Example 1. Concentration afforded the title compound (1.1 g) as a pale yellow oil and the structure verified by NMR.

Analysis for C$_{11}$H$_{21}$NO$_4$ (MW 231.3): Calcd.: C, 57.12; H, 9.15; N, 6.06. Found: C, 56.78; H, 9.18; N, 5.86.

EXAMPLE 38

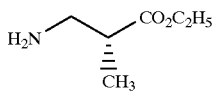

Ethyl 3-amino-2R-methylpropanoate Trifluoroacete

The title compound was prepared by the method of Example 33 using the title product of Example 37 (2.8 g, 13 mmol) instead of the title product of Example 32. Concentration afforded the trifluoroacetate salt of the title compound (1.1 g) as a pale brown liquid and the structure verified by NMR.

EXAMPLE 39

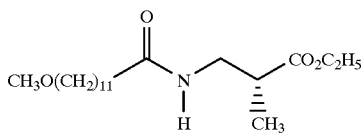

Ethyl 3-[[(12-methoxy-1-oxododecyl)amino]-2R-methyl]propanoate

The title compound was prepared by the method of Example 14 using the title product of Example 38 (1.1 g, 4.6 mmol) instead of benzylamine. Chromatography of the crude residue on silica gel using 50-50-0.5 ethyl acetate-heptane-ammonium hydroxide as eluant gave the title compound (714 mg) as a white powder, m.p. 56.8–59.5° C. The structure was supported by NMR, infrared spectroscopy, optical rotation ($[\alpha]_{365}^{25}$ −47.2°, $CHCl_3$), elemental analysis, and mass spectroscopy.

Analysis for $C_{19}H_{37}NO_4$ (MW 343.5): Calcd.: C, 66.44; H, 10.86; N, 4.08. Found: C, 66.60; H, 10.72; N, 4.06.

EXAMPLE 40

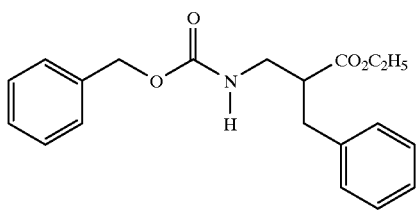

Ethyl N-(p-Methoxybenzyloxycarbonyl)-3-amino-2R (phenylmethyl)propanoate

The title compound was prepared by the method of Example 8 using ethyl iodide (0.15 mL, 2 mmol) instead of methyl iodide and N-(p-methoxybenzyloxycarbonyl)-3-amino-2S-(phenylmethyl)propanoic acid (325 mg, 1 mmol; European Patent Appln. 327,523, published Nov. 7, 1990, Example 1 and Table 1a) instead of the title product of Example 1. Concentration afforded the title compound (461 mg) as a pale yellow liquid and the structure verified by NMR.

EXAMPLE 41

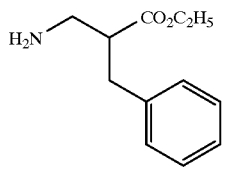

Ethyl 3-Amino-2R-(phenylmethyl)propanoate

A solution of the title product of Example 40 (260 mg, 0.73 mmol) in 26 mL of methanol was hydrogenated in the presence of 4% palladium and carbon at room temperature under a pressure of 5 pounds per square inch of hydrogen for 2 hours. The reaction was filtered to remove the catalyst and the solvent removed on a rotary evaporator to give the title compound (152 mg) as a beige paste and the structure verified by NMR.

EXAMPLE 42

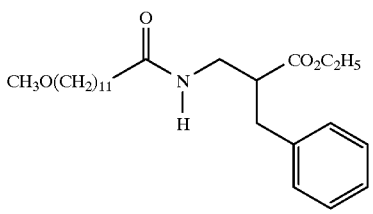

Ethyl α-[[(12-Methoxy-1-oxododecyl)amino] methyl]benzenepropanoate

The title compound was prepared by the method of Example 14 using the title product of Example 41 (152 mg, 0.75 mmol) instead of benzylamine. Chromatography of the crude residue on silica gel using 20-80 ethyl acetate-hexane as eluant gave the title compound (70 mg) as a white powder, m.p. 41.0–44.0° C. (DSC). The structure was supported by NMR, infrared spectroscopy, elemental analysis, and mass spectroscopy.

Analysis for $C_{25}H_{41}NO_4$ (MW 419.6): Calcd.: C, 71.56; H, 9.85; N, 33.34. Found: C, 71.45; H, 9.84; N, 3.30.

EXAMPLE 43

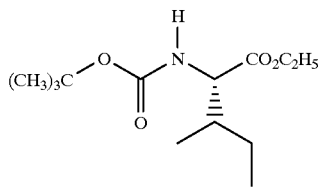

N-(t-Butyloxycarbonyl)-L-isoleucine Ethyl ester

The title compound was prepared by the method of Example 8 using ethyl iodide (0.4 mL, 5 mmol) instead of methyl iodide and BOC-L-Ile-OH-0.5 $H_2O$ (1.0 g, 4 mmol) instead of the title product of Example 1. Concentration afforded the title compound (1.1 g) as a water white liquid and the structure verified by NMR.

EXAMPLE 44

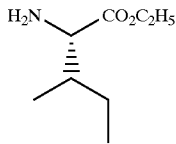

L-Isoleucine Ethyl Ester Trifluoroacete

The title compound was prepared by the method of Example 33 using the title product of Example 43 (1.1 g, 4 mmol) instead of the title product of Example 32. Concentration afforded the trifluroracetate salt of the title compound (1.3 g) as a pale yellow liquid and the structure verified by NMR.

EXAMPLE 45

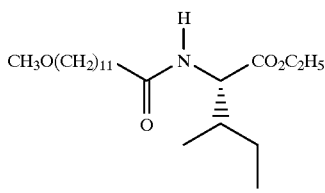

N-(12-Methoxy-1-oxododecyl)-L-isoleucine, Ethyl ester

The title compound was prepared by the method of Example 14 using the title product of Example 44 (1.1 g, 4 mmol) instead of benzylamine. Chromatography of the crude residue on silica gel using 50-50 ethyl acetate-heptane as eluant gave the title compound (875 mg) as a white powder, m.p. 36.4–38.1° C. (DSC). The structure was supported by NMR, infrared spectroscopy, optical rotation ($[\alpha]_{365}^{25}$ +81.9°, $CHCl_3$), elemental analysis, and mass spectroscopy.

Analysis for $C_{21}H_{41}NO_4$ (MW 371.6): Calcd.: C, 67.88; H, 11.12; N, 3.77. Found: C, 67.85; H, 11.25; N, 3.74.

EXAMPLE 46

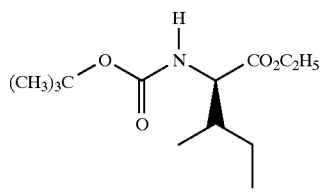

N-(t-Butyloxycarbonyl)-D-isoleucine, Ethyl ester

The title compound was prepared by the method of Example 8 using ethyl iodide (0.4 mL, 5 mmol) instead of methyl iodide and BOC-D-Ile-OH-0.5 $H_2O$ (1.0 g, 4 mmol) instead of the title product of Example 1. Concentration afforded the title compound (1.2 g) as a water white liquid and the structure verified by NMR.

EXAMPLE 47

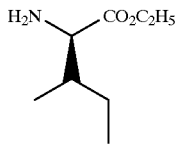

D-Isoleucine Ethyl Ester Trifluoroacete

The title compound was prepared by the method of Example 33 using the title product of Example 46 (1.1 g, 4 mmol) instead of the title product of Example 32. Concentration afforded the trifluoroacetate salt of the title compound (1.2 g) as a pale brown liquid and the structure verified by NMR.

EXAMPLE 48

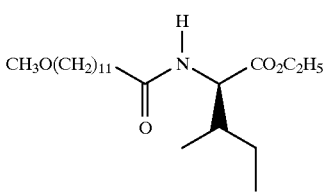

N-(12-Methoxy-1-oxododecyl)-D-isoleucine Ethyl ester

The title compound was prepared by the method of Example 14 using the title product of Example 47 (1.1 g, 4 mmol) instead of benzylamine. Chromatography of the crude residue on silica gel using 50-50 ethyl acetate-heptane as eluant gave the title compound (905 mg) as a white powder, m.p. 35.8–38.2° C. (DSC). The structure was supported by NMR, infrared spectroscopy, optical rotation ($[\alpha]_{365}^{25}$ 77.4°, $CHCl_3$), elemental analysis, and mass spectroscopy.

Analysis for $C_{21}H_{41}NO_4$ (MW 371.6): Calcd.: C, 67.88; H, 11.12; N, 3.77. Found: C, 67.64; H, 10.88; N, 3.65.

EXAMPLE 49

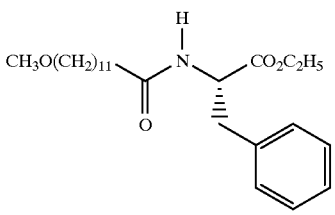

N-(12-Methoxy-1-oxododecyl)-L-phenylalanine, Ethyl ester

The title compound was prepared by the method of Example 14 using L-phenylalanine ethyl ester hydrochloride (2.0 g, 8.8 mmol) instead of benzylamine and triethylamine (1.2 mL, 8.6 mmol) instead of diisopropylethylamine. Chromatography of the crude residue on silica gel using 40-60 ethyl acetate-hexane as eluant gave the title compound (1.6 g) as a white powder, m.p. 51.0–53.4° C. The structure was supported by NMR, infrared spectroscopy, optical rotation ($[\alpha]_{365}^{25}$ +220.2°, $CHCl_3$), elemental analysis, and mass spectroscopy.

Analysis for $C_{24}H_{39}NO_4$ (MW 405.6): Calcd.: C, 71.08; H, 9.69; N, 3.45. Found: C, 71.20; H, 9.72; N, 3.43.

EXAMPLE 50

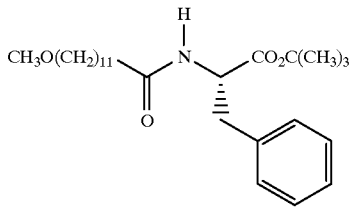

N-(12-Methoxy-1-oxododecyl)-L-phenylalanine, 1, 1-Dimethylethyl ester

The title compound was prepared by the method of Example 14 using L-phenylalanine 1,1-dimethylethyl ester (971 mg, 4.4 mmol) instead of benzylauine and triethylamine (0.61 mL, 4.4 mmol) instead of diisopropylethylamine. Chromatography of the crude residue on silica gel using 50-50 ethyl acetate-hexane as eluant gave the title compound (1.1 g) as a water white liquid. The structure was supported by NMR, infrared spectroscopy, optical rotation ($[\alpha]_{365}^{25}$ +192.8°, $CHCl_3$), elemental analysis, and mass spectroscopy.

Analysis for $C_{26}H_{43}NO_4$ (MW 433.6): Calcd.: C, 72.02; H, 10.00; N, 3.23. Found: C, 71.62; H. 10.20; N, 3.13.

EXAMPLE 51

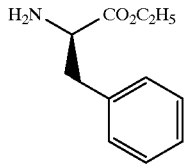

D-Phenylalanine Ethyl ester p-Toluenesulfonate

A mixture of D-phenylalanine (5.0 g, 30 mmol) and p-toluenesulfonic acid monohydrate (12.7 g, 67 mmol) in 150 mL of anhydrous ethanol was refluxed for 24 hours. After cooling to room temperature, the solvent was removed by rotary evaporator, the residue triturated with diethyl ether, filtered and dried in vacuo over $P_2O_5$ to give the p-toluenesulfonate salt of the title compound (9.7 g) as a white solid and the structure verified by NMR.

EXAMPLE 52

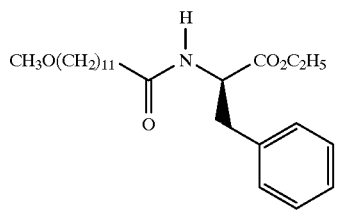

N-(12-Methoxy-1-oxododecyl)-D-phenylalanine, Ethyl ester

The title compound was prepared by the method of Example 14 using the title product of Example 51 (3.3 g, 8.9 mmol) instead of benzylamine and triethylamine (2.5 mL, 18 mmol) instead of diisopropylethylamine. Chromatography of the crude residue on silica gel using 25-75 ethyl acetate-hexane as eluant gave the title compound (2.4.g) as a white solid, m.p. 51.0–53.1° C. (DSC). The structure was supported by NMR, infrared spectroscopy, optical rotation ($[\alpha]_{365}^{25}$ −221.8°, $CHCl_3$), elemental analysis, and mass spectroscopy.

Analysis for $C_{24}H_{39}NO_4$ (MW 405.6): Calcd.: C, 71.08; H, 9.69; N, 3.45. Found: C, 71.08; H, 9.86; N, 3.42.

EXAMPLE 53

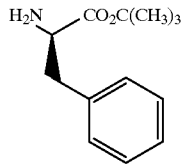

D-Phenylalanine 1,1-Dimethylethyl ester

To a solution of D-phenylalanine (5.5 g, 33 mmol) in 430 mL of t-butyl acetate was added concentrated perchloric acid (2 mL, 33 mmol). After stirring at room temperature, the reaction mixture was filtered and the filter cake washed with copious diethyl ether. The filter cake was suspended in diethyl ether and washed with two portions of 5% citric acid. The acid washes were combined, neutralized with solid $NaHCO_3$ and extracted with two portions of diethyl ether. The combined organic extracts were washed with brine, dried with magnesium sulfate and concentrated to give the title compound (404 mg) as a pale yellow liquid and the structure verified by NMR.

EXAMPLE 54

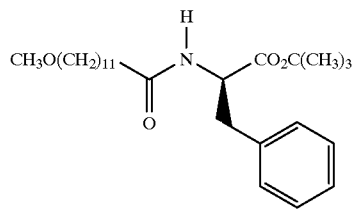

N-(12-Methoxy-1-oxododecyl)-D-phenylalanine, 1, 1Dimethylethyl ester

The title compound was prepared by the method of Example 14 using the title product of Example 53 (292 mg, 1.3 mmol) instead of benzylamine and triethylamine (0.2 mL, 1.4 mmol) instead of diisopropylethylamine. Chromatography of the crude residue on silica gel using 25-75 ethyl acetate-hexane as eluant gave the title compound (496 mg) as a pale yellow liquid. The structure was supported by NMR, infrared spectroscopy, optical rotation ($[\alpha]_{365}^{25}$ −188.2°, $CHCl_3$), elemental analysis, and mass spectroscopy.

Analysis for $C_{26}H_{43}NO_4$ (MW 433.6): Calcd.: C, 72.02; H, 10.00; N, 3.23. Found: C, 71.20; H, 9.96; N. 3.13.

EXAMPLE 55

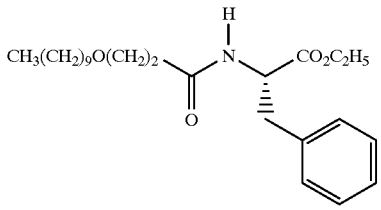

N-(3-(Decycloxy)-1-oxopropyl]-L-phenylalanine, Ethyl ester

The title compound was prepared by the method of Example 19 using the L-phenylalanine ethyl ester hydrochloride (214 mg, 0.93 mmol) instead of diethylamine. Radial chromatography of the crude residue on silica gel using 20-80 ethyl acetate-hexane as eluant gave the title compound (329 mg) as a white solid, m.p. 50.3–52.4° C. (DSC). The structure was supported by NMR, infrared spectroscopy, optical rotation ($[\alpha]_{365}^{25}$ +180.6°, $CHCl_3$), elemental analysis, and mass spectroscopy.

Analysis for $C_{24}H_{39}NO_4$ (MW 405.6): Calcd.: C, 71.08; H, 9.69; N, 3.45. Found: C, 70.88; H, 9.81; N, 3.38.

EXAMPLE 56

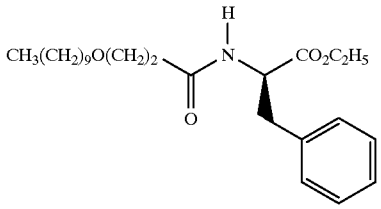

N-(3-(Decyloxy)-1-oxoproyl[-D-phenylalanine, Ethyl ester

The title compound was prepared by the method of Example 19 using the title product of Example 51 (348 mg, 0.95 mmol) instead of diethylamine. Radial chromatography of the crude residue on silica gel using 20-80 ethyl acetate-hexane as eluant gave the title compound (275 mg) as a white solid, m.p. 51.4–54.7° C. (DSC). The structure was supported by NMR, infrared spectroscopy, elemental analysis, optical rotation ($[\alpha]_{365}^{25}$ −178.3, $CHCl_3$) and mass spectroscopy.

Analysis for $C_{24}H_{39}NO_4$ (MW 405.6): Calcd.: C, 71.08; H, 9.69; N, 3.45. Found: C, 70.96; HI 9.61; N. 3.41.

EXAMPLE 57

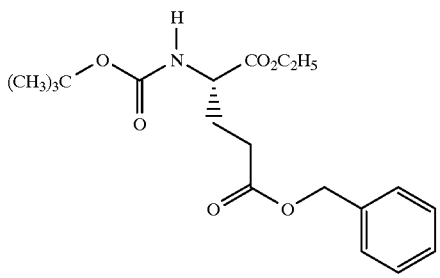

N-(t-Butyloxycarbonyl)-L-glutamic acid, 1-Ethyl 5-(Phenylmethyl) ester

The title compound was prepared by the method of Example 8 using ethyl iodide (0.3 mL, 3.8 mmol) instead of methyl iodide and BOC-L-Glu(O-benzyl)-OH (1.0 g, 3.1 mmol) instead of the title product of Example 1. Concentration afforded the title compound (1.1 g) as a white wax and the structure verified by NMR.

EXAMPLE 58

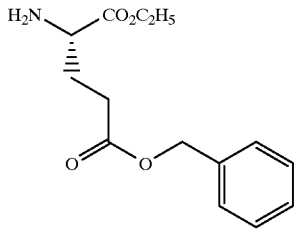

L-glutamic acid, 1-Ethyl 5-(Phenylmethyl) ester Trifluoroacetate

The title compound was prepared by the method of Example 33 using the title product of Example 57 (1.1 g, 4 mmol) instead of the title product of Example 32. Concentration afforded the trifluoroacetate salt of the title compound (1.2 g) as a pale brown liquid and the structure verified by NMR.

EXAMPLE 59

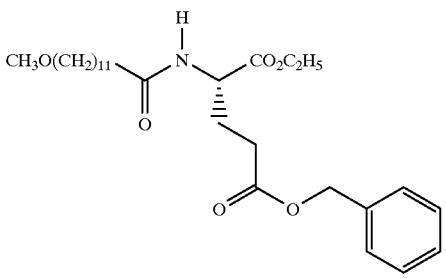

N-(12-methoxy-1-oxododecyl)-L glutamic acid, 1-Ethyl 5-(Phenylmethyl) ester

The title compound was prepared by the method of Example 14 using the title product of Example 58 (1.1 g, 2.9 mmol) instead of benzylamine. Chromatography of the crude residue on silica gel using 50-50 ethyl acetate-heptane as eluant gave the title compound (942 mg) as a pale yellow solid, m.p. 42.7–45.0° C. (DSC). The structure was supported by NMR, infrared spectroscopy, optical rotation ($[\alpha]_{365}^{25}$ +57.7°, $CHCl_3$), elemental analysis, and mass spectroscopy.

Analysis for $C_{27}H_{43}NO_6$ (MW 477.6): Calcd.: C, 67.90; H, 9.07; N, 2.93. Found: C, 66.68; H, 8.99; N, 2.96.

EXAMPLE 60

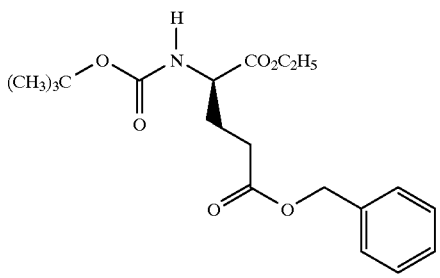

N-(t-Butyloxycarbonyl)-D-glutamic acid, 1-Ethyl 5-(Phenylmethyl) ester

The title compound was prepared by the method of Example 8 using ethyl iodide (0.3 mL, 3.8 mmol) instead of methyl iodide and BOC-D-Glu(O-benzyl)-OH (1.0 g, 3.0 mmol) instead of the title product of Example 1. Concentration afforded the title compound (1.1 g) as a yellow liquid and the structure verified by NMR.

EXAMPLE 61

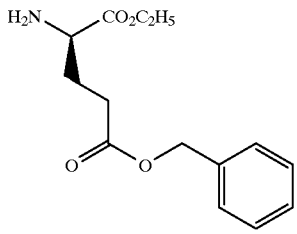

D-glutamic acid, 1-Ethyl 5-(Phenylmethyl) ester Trifluoroacetate

The title compound was prepared by the method of Example 33 using the title product of Example 60 (1.1 g, 3 mmol) instead of the title product of Example 32. Concentration afforded the trifluoroacetic salt of the title compound (1.1 g) as a pale brown liquid and the structure verified by NMR.

EXAMPLE 62

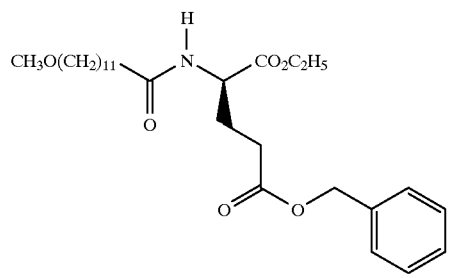

N-(12-methoxy-1-oxododecyl)-D-glutamic acid, 1-Ethyl 5-(Phenylmethyl) ester

The title compound was prepared by the method of Example 14 using the title product of Example 61 (1.1 g, 2.9 mmol) instead of benzylamine. Chromatography of the crude residue on silica gel using 50-50 ethyl acetate-heptane as eluant gave the title compound (839 mg) as a pale yellow solid, m.p. 38.4–42.1° C. (DSC). The structure was supported by NMR, infrared spectroscopy, optical rotation ($[\alpha]_{365}^{25}$ −54.0°, $CHCl_3$), elemental analysis, and mass spectroscopy.

Analysis for $C_{27}H_{43}NO_6$ (MW 477.6): Calcd.: C, 67.90; H, 9.07; N, 2.93. Found: C, 67.43; H, 9.27; N, 2.97.

EXAMPLE 63

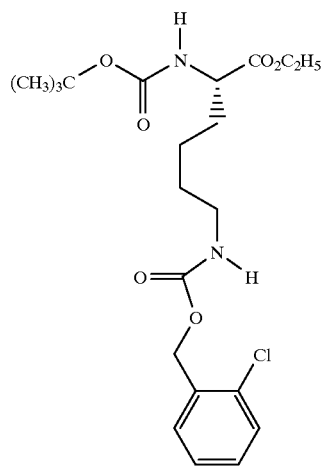

N-[[2-Chlorophenyl)methoxy]carbonyl]-N2-[t-butyloxycarbonyl]-L-lysine, Ethyl ester The title compound was prepared by the method of Example 8 using ethyl iodide (0.24 mL, 3.0 mmol) instead of methyl iodide and BOC-L-Lys ([(2-chlorophenyl)methoxy]carbonyl)-OH (1.0 g, 2.5 mmol) instead of the title product of Example 1. Concentration afforded the title compound (1.1 g) as a yellow liquid and the structure verified by NMR.

EXAMPLE 64

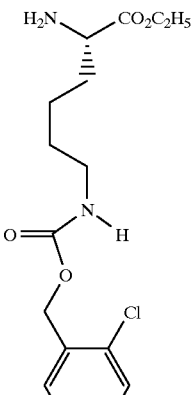

N6-[[(2-Chlorophenyl)methoxy]carbonyl]-L-lysine, Ethyl ester Trifluoroacetate

The title compound was prepared by the method of Example 33 using the title product of Example 63 (1.1 g, 2.5 mmol) instead of the title product of Example 32. Concentration afforded the trifluoroacetate salt of the title compound (1.2 g) as a pale brown liquid and the structure verified by NMR.

EXAMPLE 65

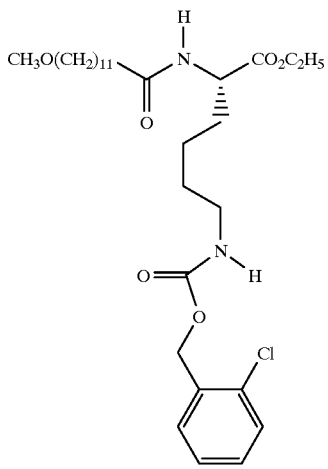

N6-[[(2-Chlorophenyl)methoxy]carbonyl]-N2-(12-methoxy-1oxododecyl)-L-lysine, Ethyl ester The title compound was prepared by the method of Example 14 using the title product of Example 64 (1.2 g, 2.6 mmol) instead of benzylamine. Chromatography of the crude residue on silica gel using 50-50 ethyl acetate-heptane as eluant gave the title compound (642 mg) as a pale yellow solid, m.p. 62.0–64.2° C. (DSC). The structure was supported by NMR, infrared spectroscopy, optical rotation ($[\alpha]_{365}^{25}$ +39.2°, $CHCl_3$), elemental analysis, and mass spectroscopy.

Analysis for $C_{29}H_{47}N_2O_6Cl$ (MW 555.2): Calcd.: C, 62.74; H, 8.53; N, 5.05; Cl, 6.39. Found: C, 62.74; H, 8.44; N, 5.07; Cl, 6.41.

EXAMPLE 66

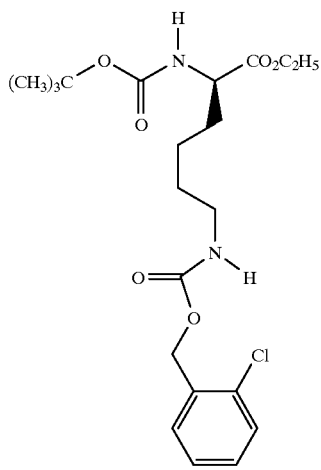

N6-[[(2-Chlorophenyl)methoxy]carbonyl]-N2-[t-butyloxycarbonyl]-D-lysine, Ethyl ester The title compound was prepared by the method of Example 8 using ethyl iodide (0.18 mL, 2.2 mmol) instead of methyl iodide and BOC-D-Lys([(2-chlorophenyl)methoxy]carbonyl)-OH t-butylamine (1.0 g, 1.8 mmol) instead of the title product of Example 1. Concentration afforded the title compound (717 mg) as a yellow oil and the structure verified by NMR.

EXAMPLE 67

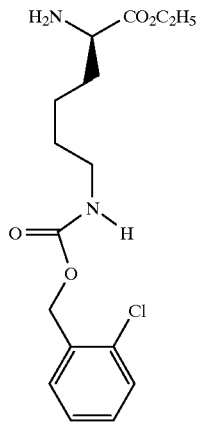

N6-[[(2-Chlorophenyl)methoxy]carbonyl-D-lysine, Ethyl ester Trifluoroacetate

The title compound was prepared by the method of Example 33 using the title product of Example 66 (717 mg, 1.6 mmol) instead of the title product of Example 32. Concentration afforded the trifluoroacetate salt of the title compound (765 mg) as a pale brown liquid and the structure verified by NMR.

EXAMPLE 68

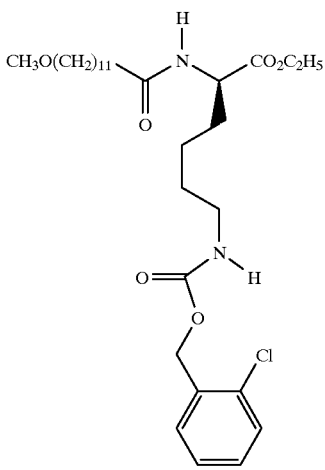

N6-[[(2-Chlorophenyl)methoxy]carbonyl]-N2-(12-methoxy-1-oxododecyl)-D-lysine, Ethyl ester The title compound was prepared by the method of Example 14 using the title product of Example 68 (740 mg, 1.7 mmol) instead of benzylamine. Chromatography of the crude residue on silica gel using 50-50 ethyl acetate-heptane as eluant gave the title compound (596 mg) as a white solid, m.p. 62.4–64.2° C. (DSC). The structure was supported by NMR, infrared spectroscopy, optical rotation ($[\alpha]_{365}^{25}$ −41.8°, CHCl$_3$), elemental analysis, and mass spectroscopy.

Analysis for C$_{29}$H$_{47}$N$_2$O$_6$Cl (MW 555.2): Calcd.: C, 62.74; H, 8.53; N, 5.05; Cl, 6.39. Found: C, 62.60; H, 8.52; N, 5.00; Cl, 6.39.

EXAMPLE 69

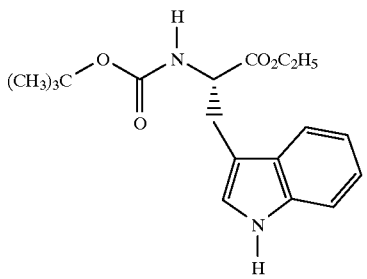

N-(t-Butyloxycarbonyl)-L-tryptophan, Ethyl ester

The title compound was prepared by the method of Example 8 using ethyl iodide (0.35 mL, 4.4 mmol) instead of methyl iodide and BOC-L-Trp-OH (1.1 g, 3.6 mmol) instead of the title product of Example 1. Concentration afforded the title compound (1.2 g) as a yellow oil and the structure verified by NMR.

EXAMPLE 70

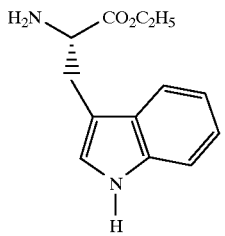

L-Tryptophan Ethyl ester Trifluoroacetate

The title compound was prepared by the method of Example 33 using the title product of Example 69 (1.2 g, 3.5 mmol) instead of the title product of Example 32. Concentration afforded the trifluoroacetate salt of the title compound (1.2 g) as a pale brown liquid and the structure verified by NMR.

EXAMPLE 71

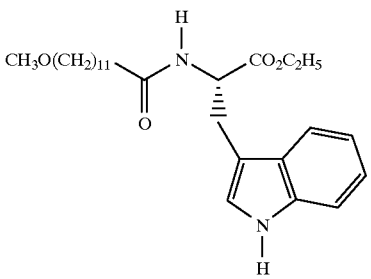

N-(12-Methoxy-1-oxododecyl)-L-tryptophan, Ethyl ester

The title compound was prepared by the method of Example 14 using the title product of Example 70 (1.2 g, 3.5 mmol) instead of benzylamine. Chromatography of the crude residue on silica gel using 50-50 ethyl acetate-heptane as eluant gave the title compound (671 mg) as a pale yellow paste. The structure was supported by NMR, infrared spectroscopy, optical rotation ($[\alpha]_{365}^{25}$ +155.9°, CHCl$_3$), elemental analysis, and mass spectroscopy.

Analysis for C$_{26}$H$_{40}$N$_2$O$_4$ (MW 444.6): Calcd.: C, 70.24; H, 9.07; N, 6.30. Found: C, 70.08; H, 9.20; N, 6.27.

EXAMPLE 72

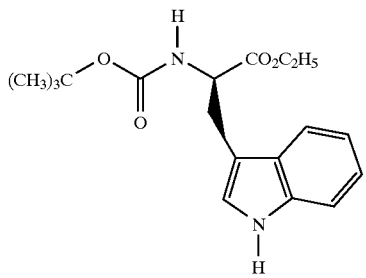

N-(t-Butyloxycarbonyl)-D-tryptophan, Ethyl ester

The title compound was prepared by the method of Example 8 using ethyl iodide (0.35 mL, 4.4 mmol) instead of methyl iodide and BOC-D-Trp-OH (1.0 g, 3.3 mmol) instead of the title product of Example 1. Concentration afforded the title compound (1.1 g) as a white solid and the structure verified by NMR.

EXAMPLE 73

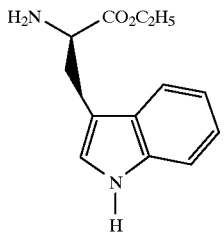

D-Tryptophan, Ethyl ester Trifluoroacetate

The title compound was prepared by the method of Example 33 using the title product of Example 72 (1.1 g, 3.3 mmol) instead of the title product of Example 32. Concentration afforded the trifluoroacetate salt of the title compound (1.2 g) as a pale brown liquid and the structure verified by NMR.

EXAMPLE 74

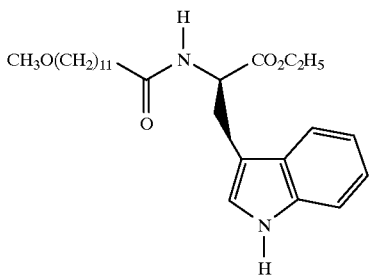

N-(12-Methoxy-1-oxododecyl)-D-tryptophan, Ethyl ester

The title compound was prepared by the method of Example 14 using the title product of Example 73 (1.2 g, 3.5 mmol) instead of benzylamine. Chromatography of the crude residue on silica gel using 50-50 ethyl acetate-heptane as eluant gave the title compound (650 mg) as a yellow oil. The structure was supported by NMR, infrared spectroscopy, optical rotation ($[\alpha]_{365}^{25}$ −156.2°, CHCl$_3$), elemental analysis, and mass spectroscopy.

Analysis for C$_{26}$H$_{40}$N$_2$O$_4$ (MW 444.6): Calcd.: C, 70.24; H, 9.07; N, 6.30. Found: C, 69.24; H, 9.13; N, 6.12.

EXAMPLE 75

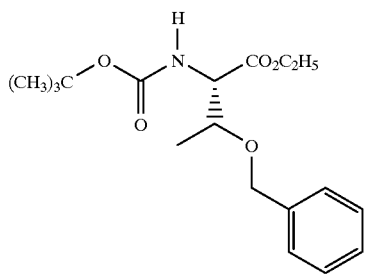

N-(t-Butyloxycarbonyl)-O-(phenylmethyl)-L-threonine, Ethyl ester

The title compound was prepared by the method of Example 8 using ethyl iodide (0.31 mL, 3.9 mmol) instead of methyl iodide and BOC-L-Thr-(O-benzyl)-OH (1.0 g, 3.4 mmol) instead of the title product of Example 1. Concentration afforded the title compound (818 mg) as a water-white liquid and the structure verified by NMR.

EXAMPLE 76

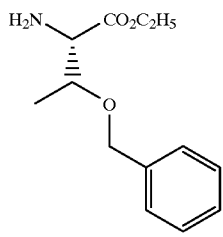

O-(Phenylmethyl)-L-threonine, Ethyl ester Trifluoroacetate

The title compound was prepared by the method of Example 33 using the title product of Example 75 (818 mg, 2.4 mmol) instead of the title product of Example 32. Concentration afforded the trifluoroacetate salt of the title compound (821 mg) as a pale brown liquid and the structure verified by NMR.

EXAMPLE 77

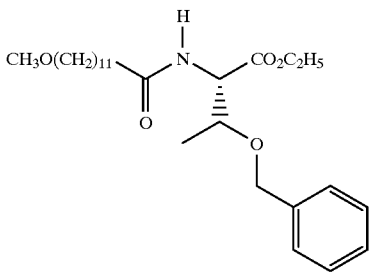

N-(12-methoxy-1-oxododecyl)-O-(phenylmethyl)-L-threonine, Ethyl ester

The title compound was prepared by the method of Example 14 using the title product of Example 76 (821 mg, 2.3 mmol) instead of benzylamine. Chromatography of the crude residue on silica gel using 50-50 ethyl acetate-heptane as eluant gave the title compound (632 mg) as a white solid, m.p. 42.9 –46.9° C. (DSC). The structure was supported by NMR, infrared spectroscopy, optical rotation ($[\alpha]_{365}^{25}$ +36.0°, CHCl$_3$), elemental analysis, and mass spectroscopy.

Analysis for C$_{26}$H$_{43}$NO$_5$ (MW 449.6): Calcd.: C, 69.45; H, 9.64; N, 3.12. Found: C, 69.20; H, 9.52; N, 3.13.

EXAMPLE 78

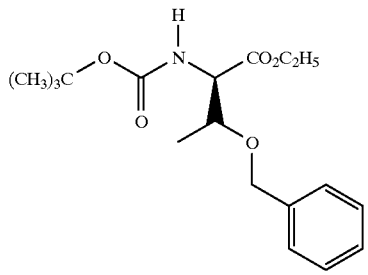

N-(t-Butyloxycarbonyl)-O-(phenylmethyl)-D-threonine, Ethyl ester

The title compound was prepared by the method of Example 8 using ethyl iodide (0.31 mL, 3.9 mmol) instead of methyl iodide and BOC-D-Thr-(O-benzyl)-OH (1.0 g, 3.2 mmol) instead of the title product of Example 1. Concentration afforded the title compound (1.0 g) as a yellow liquid and the structure verified by NMR.

EXAMPLE 79

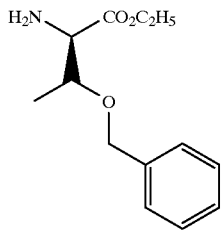

O(phenylmethyl)-D-threonine, Ethyl ester Trifluoroacetate

The title compound was prepared by the method of Example 33 using the title product of Example 78 (1.0 g, 3.0 mmol) instead of the title product of Example 32. Concentration afforded the trifluoroacetate salt of the title compound (919 mg) as a pale brown liquid and the structure verified by NMR.

EXAMPLE 80

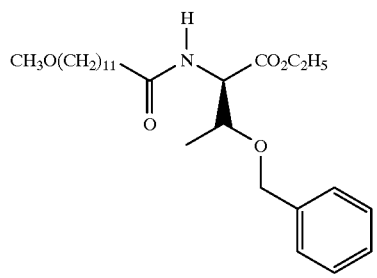

N-(12-methoxy-1-oxododecyl)-O-(phenylmethyl)-D-threonine, Ethyl ester

The title compound was prepared by the method of Example 14 using the title product of Example 79 (919 mg, 2.6 mmol) instead of benzylamine. Chromatography of the crude residue on silica gel using 50-50 ethyl acetate-heptane as eluant gave the title compound (755 mg) as a white flaky solid, m.p. 38.1–47.0° C. (DSC). The structure was supported by NMR, infrared spectroscopy, optical rotation ($[\alpha]_{365}^{25}$ –37.0°, CHCl$_3$), elemental analysis, and mass spectroscopy.

Analysis for C$_{26}$H$_{43}$NO$_5$ (MW 449.6): Calcd.: C, 69.45; H, 9.64; N, 3.12. Found: C, 69.19; H, 9.59; N, 3.16.

EXAMPLE 81

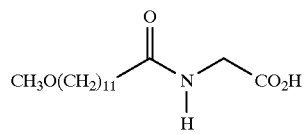

N-(12-Methoxy-1-oxodecyl)glycine

To the title product of Example 23 (321 mg, 0.93 mmol) in 1 mL of dioxane was added dropwise a solution of hydrochloric acid in dioxane (1 mL, 4M). After stirring at room temperature, the solvent was removed by rotary evaporator and the resulting residue was taken up in anhydrous toluene and concentrated to give the title compound (254 mg) as a white solid m.p. 103.1–104.7° C. (DSC). The structure was supported by NMR, elemental analysis, and mass spectroscopy.

Analysis for C$_{15}$H$_{29}$NO$_4$ (MW 287.4): Calcd.: C, 62.69; H, 10.19; N, 4.87. Found: C, 62.37; H, 10.19; N, 4.80.

EXAMPLE 82

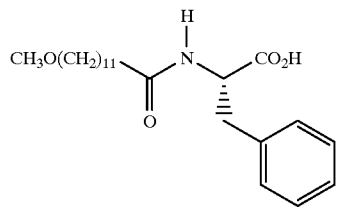

N-(12-Methoxy-1-oxododecyl)-L-phenylalanine

The title compound was prepared by the method of Example 81 using the title product of Example 50 (301 mg, 0.69 mmol) instead of the title product of Example 23. Chromatography of the crude residue on silica gel using 50-50-1 ethyl acetate-heptane-acetic acid as eluant gave the title compound (172 mg) as a white powder, m.p. 73.3–77.3° C. (DSC). The structure was supported by NMR, infrared spectroscopy, optical rotation ($[\alpha]_{365}^{25}$ +226.0°, CHCl$_3$), and elemental analysis.

Analysis for C$_{22}$H$_{35}$NO$_4$ (MW 377.5): Calcd.: C, 69.99; H, 9.34; N, 3.71. Found: C, 69.83; H, 8.94; N, 3.65.

EXAMPLE 83

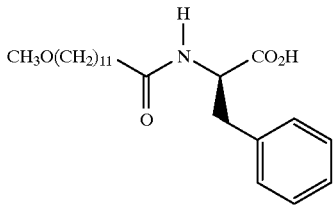

N-(12-Methoxy-1-oxododecyl)-D-phenylalanine

The title compound was prepared by the method of Example 81 using the title product of Example 54 (135 mg, 0.31 mmol) instead of the title product of Example 23. Chromatography of the crude residue on silica gel using 50-50-1 ethyl acetate-heptane-acetic acid as eluant gave the title compound (83 mg) as a white powder, m.p. 69.3–72.8° C. The structure was supported by NMR, infrared spectroscopy, optical rotation ($[\alpha]_{365}^{25}$ −222.9°, CHCl$_3$), and elemental analysis.

Analysis for C$_{22}$H$_{35}$NO$_4$ (MW 377.5): Calcd.: C, 69.99; H, 9.34; N, 3.71. Found: C, 69.67; H, 9.35; N, 3.65.

EXAMPLE 84

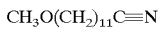

12-Methoxydodecanenitrile

To the title compound of Example 12 (5.0 g, 22 mmol) in 30 mL pyridine at 0° C. was added in portions p-toluenesulfonyl chloride (5.1 g, 27 mmol). After stirring at room temperature for 3 days, the reaction mixture was filtered, the cake washed with methylene chloride and the filtrate concentrated. The resulting residue was dissolved in methylene chloride, washed successively with 1N HCl, water, saturated NaHCO$_3$, water and brine, dried with magnesium sulfate, filtered and concentrated. Chromatography of the crude product on silica gel using 20-80 diethyl ether-hexane as eluant gave the title compound (3.4 g) as a pale yellow liquid. The structure was supported by NMR, infrared spectroscopy, elemental analysis and mass spectroscopy.

Analysis for C$_{13}$H$_{25}$NO (MW 211.4): Calcd.: C, 73.88; H, 11.92: N, 6.63. Found: C, 73.57; H, 12.07; N, 6.41.

EXAMPLE 85

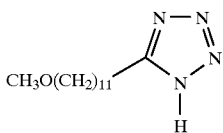

5-(11-Methoxyundecyl)-1H-tetrazole

To the title compound of Example 84 (1.0 g, 4.8 mmol) in 10 mL of toluene at room temperature was added successively sodium azide (929 mg, 14 mmol), lithium chloride (596 mg, 14 mmol) and chlorotributyltin (1.5 mL, 5.5 mmol). The heterogeneous mixture was refluxed for two days, diluted with 10 mL toluene and refluxing continued for 24 hours. After cooling to room temperature, the reaction mixture was filtered and the cake washed with copious toluene. The resulting white cake was dissolved in water, acidified to pH 6 with 1N HCl and extracted with three portions of methylene chloride. The combined organic extracts were washed with brine, dried with magnesium sulfate and concentrated to give the title compound (600 mg) as a white powder, m.p. 66.3–68.3° C. (DSC). The structure was supported by NMR, infrared spectroscopy, elemental analysis and mass spectroscopy.

Analysis for C$_{13}$H$_{26}$N$_4$O (MW 254.4): Calcd.: C, 61.38; H, 10.30; N, 22.05. Found: C, 61.25; H, 10.53; N, 21.83.

EXAMPLE 86

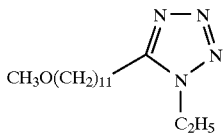

A. 1-Ethyl-5-(11-methoxyundecyl)-1H-tetrazole

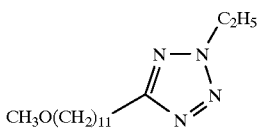

B. 2-Ethyl-5-(11-methoxyundecyl)-2H-tetrazole

Sodium hydride dispersed in mineral oil (192 mg, 4.8 mmol; washed three times with hexane) was treated with the title product of Example 85 (1.1 g, 4.2 mmol) in 10 mL of dimethylformamide for 16 hours at room temperature followed by the addition of ethyl iodide (0.38 mL, 4.8 mmol). After stirring at room temperature for 24 hours, the solvent was removed by rotary evaporator and the resulting residue partioned between ethyl acetate and water and the aqueous phase extracted with ethyl acetate. The combined organic phases were washed with water and brine, dried with magnesium sulfate and concentrated. Chromatography of the crude residue on silica gel using 25-75 ethyl acetate-hexane gave title compound B (674 mg) as a pale yellow liquid and title compound A (414 mg) as a white powder, m.p. 51.0–52.8° C. (DSC). Both structures were supported by NMR, infrared spectroscopy, elemental analysis and mass spectroscopy.

Analysis for A: $C_{15}H_{30}N_4O$ (MW 282.4): Calcd.: C, 63.79; H, 10.71; N, 19.84. Found: C, 63.82; H, 10.76; N, 19.75.

Analysis for B: $C_{15}H_{30}N_4O$ (MW 282.4): Calcd.: C, 63.79; H, 10.71; N, 19.84. Found: C, 63.66; H, 10.61; N, 19.74.

EXAMPLE 87

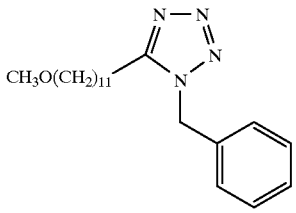

A. 5-(11-Methoxyundecyl)-1-(phenylmethyl)-1H-tetrazole

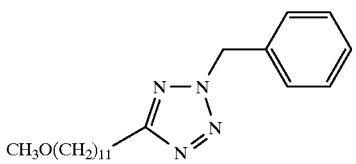

B. 5-(11-Methoxyundecyl)-2-(phenylmethyl)-2H-tetrazole

The title compounds were prepared by the method of Example 86 using benzylbromide (1.1 mL, 9.3 mmol) instead of ethyl iodide. Chromatography of the crude residue on silica gel using 40-60 ethyl acetate-hexane gave title compound B (1.1 g) as a pale yellow liquid and title compound A (1.5 g) as a white powder, m.p. 58.8–60.8° C. (DSC). Both structures were supported by NMR, infrared spectroscopy, elemental analysis and mass spectroscopy.

Analysis for A: $C_{20}H_{32}N_4O$ (MW 344.5): Calcd.: C, 69.73; H, 9.36; N, 16.26. Found: C, 69.77; H, 9.69; N, 16.45.

Analysis for B: $C_{20}H_{32}N_4O$ (MW 344.5): Calcd.: C, 69.73; H, 9.36; N, 16.26. Found: C, 70.26; H, 9.64; N, 15.75.

EXAMPLE 88

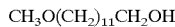

12-Methoxydodecanol

The title compound was prepared by the method of Example 3 using the title product of Example 1 (3 g, 13 mmol) instead of the title product of Example 2. Chromatography by of the crude residue on silica gel using 50-50 ethyl acetate heptane gave the title compound (2.2 g) as a white powder, m.p. 32.6–36.7° C. (DSC). The structure was supported by NMR, infrared spectroscopy, elemental analysis and mass spectroscopy.

Analysis for $C_{13}H_{28}O_2$ (MW 216.4): Calcd.: C, 72.17; H, 13.01. Found: C, 72.27; H, 13.25.

EXAMPLE 89

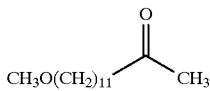

13-Methoxy-2-tridecanone

To the title product of Example 84 (516 mg, 2.4 mmol) in 10 mL of anhydrous diethyl ether was added dropwise a solution of methylmagnesium bromide in diethyl ether (1.2 mL, 3.2M) at room temperature. After refluxing for 5 days, the reaction was cooled to room temperature, poured into aqueous 1N HCl and stirred vigorously for 3 days. The layers were separated and the aqueous phase extracted with one portion each of diethyl ether and ethyl acetate. The combined organic extracts were washed with saturated $NaHCO_3$, water and brine, dried with magnesium sulfate and concentrated. Chromatography by of the crude residue on silica gel using 20-80 ethyl acetate heptane gave the titile compound (311 mg) as a yellow-brown liquid. The structure was supported by NMR, infrared spectroscopy, and elemental analysis.

Analysis for $C_{14}H_{28}O_2$ (MW 228.4): Calcd.: C, 73.63; H, 12.36. Found: C, 73.34; H, 12.23.

EXAMPLE 90

When 11-(ethylthio)undecanoic acid is substituted for an equivalent amount of 12-methoxydodecanoic acid in Example 11 and then the resulting 11-(ethylthio)undecanoyl chloride is substituted for an equivalent amount of 12-methoxydodecanoyl chloride in Example 12, the compound 11-(ethylthio)undecanamide is prepared and can be used in place of the 12-methoxydodecanamide with substantially similar antiviral results.

EXAMPLE 91

When 5-(octylthio)pentanoic acid is substituted for an equivalent amount of 12-methoxydodecanoic acid in Example 11 and then the resulting 5-(octylthio)pentanoyl chloride is substituted for an equivalent amount of 12-methoxydodecanoyl chloride in Example 12, the compound 5-(octylthio)pentanamide is prepared and can be used in place of the 12-methoxydodecanamide with substantially similar antiviral results.

EXAMPLE 92

When 6,12-dithiatetradecanoic acid is substituted for an equivalent amount of 12-methoxydoecanoic acid in Example 11 and then the resulting 6,12-dithiatetradecanoyl chloride is substituted for an equivalent amount of the 12-methoxydodecanoyl chloride in Example 12, the compound 6,12-dithiatetradecanamide is prepared and can be used in place of the 12-methoxydodecanamide with substantially similar antiviral results.

EXAMPLE 93

When any of 12-azidododecanoic acid or 12-(tetrazolyl) dodecanoic acid or 12-(triazolyl)dodecanoic acid are substituted for an equivalent amount of 12-methoxydodecanoic acid in Example 11 and then the resulting acyl chloride products are substituted for an equivalent amount of the 12-methoxydodecanoyl chloride of Example 12, the compounds 12-azidododecanamide, 12-(tetrazolyl) dodecanamide and 12-(triazolyl)dodecanamide, respectively, are prepared and can be used in place of the 12-methoxydodecanamide with substantially similar antiviral results.

EXAMPLE 94

When any of the acyl chloride products prepared in Examples 90–93 are substituted for an equivalent amount of the 12-methoxydodecanoyl chloride in Example 14, the resulting 11-(ethylthio)-N-(phenylmethyl)undecanamide or 5-(octylthio)-N-(phenylmethyl)pentanamide or 6,12-dithia-α-N-(phenylmethyl)tetradecanamide or 12-azido-N-(phenylethyl)dodecanamide or 12-(tetrazolyl-N-(phenylmethyl)dodecanamide or 12-(triazolyl)-N-(phenylmethyl)dodecanamide, respectively, are prepared and can be used in place of the 12-methoxy-N-(phenylmethyl)dodecanamide with substantially similar antiviral results.

EXAMPLE 95

When Example 94 is repeated except that the procedure of Example 50 is employed whereby L-phenylalanine 1,1-dimethylethyl ester and triethylamine are used as reactants instead of benzylamine and diisopropylethylamine, respectively, the corresponding N-(L-phenylalanine dimethylethyl ester) amides are prepared instead of the N-(phenylmethyl) amides and can be used in place of N-(12-methoxy-1-oxododecyl)-L-phenylalanine, 1,1-dimethyl ester with substantially similar antiviral results.

EXAMPLE 96

Various illustrative compounds synthesized above were tested for inhibition of HIV-1 in a test which measured reduction of cytopathogenic effect in virus-infected syncytium-sensitive Leu-3a-positive CEM cells grown in tissue culture as follows:

Tissue culture plates were incubated at 37° C. in a humidified, 5% $CO_2$ atmosphere and observed microscopically for toxicity and/or cytopathogenic effect (CPE). At 1 hour prior to infection each test article was prepared from the frozen stock, and a 20 μl volume of each dilution (prepared as a 10× concentration) was added to the appropriate wells of both infected and uninfected cells.

Assays were done in 96-well tissue culture plates. CEM cells were treated with polybrene at a concentration of 2 μg/ml, and an 80 μl volume of cells (1×10⁴ cells) was dispensed into each well. A 100 μl volume of each test article dilution (prepared as a 2× concentration) was added to 5 wells of cells, and the cells were incubated at 37° C. for 1 hour. A frozen culture of HIV-1, strain HTVL-III$_B$, was diluted in culture medium to a concentration of 5×10⁴ TCID$_{50}$ per ml, and a 20 μl volume (containing 10³ TCID$_{50}$ of virus) was added to 3 of the wells for each test article concentration. This resulted in a multiplicity of infection of 0.1 for the HIV-1 infected samples. A 20 μl volume of normal culture medium was added to the remaining wells to allow evaluation of cytotoxicity. Each plate contained 6 wells of untreated, uninfected, cell control samples and 6 wells of untreated, infected, virus control samples.

On the 7th to 9th day post-infection, the cells in each well were resuspended and a 100 μl sample of each cell suspension was removed for use in an MTT assay. A 20 μl volume of a 5 mg/ml solution of 3-(4,5-dimethylthiazol-2-yl)-2,5-diphenyltetrazolium bromide (MTT) was added to each 100 μl cell suspension, and the cells were incubated at 37° C. in 5% $CO_2$ for 4 hours. During this incubation MTT is metabolically reduced by living cells, resulting in the production of a colored formazan product. A 100 μl volume of a solution of 10% sodium dodecyl sulfate in 0.01N hydrochloric acid was added to each sample, and the samples were incubated overnight. The absorbance at 590 nm was determined for each sample using a Molecular Devices V$_{max}$ microplate reader. This assay detects drug-induced suppression of viral CPE, as well as drug cytotoxicity, by measuring the generation of MTT-formazan by surviving cells.

The following Table I, below, set forth the test results of the foregoing assay for HIV inhibition by illustrative compounds prepared in the foregoing examples.

TABLE I

HIV ACTIVITY OF FATTY ACID ANALOGS AND PRODRUGS

| Example # | EC$_{50}$ (μM) |
|---|---|
| 1 | 4.3 |
| 5 | >430 |
| 6 | >470 |
| 7 | 18.7 |
| 8 | 6.1 |
| 9 | 16.6 |
| 12 | 192 |
| 13 | >400 |
| 14 | 3.8 |
| 15 | >350 |
| 16 | 4.5 |
| 17 | 8.2 |
| 18 | >285 |
| 19 | >350 |
| 20 | >310 |
| 21 | 8.6 |
| 22 | >245 |
| 23 | 9.3 |
| 24 | >260 |
| 25 | >240 |
| 26 | >300 |
| 80 | >225 |
| 81 | 27.5 |
| 82 | 13 |
| 83 | >265 |
| 84 | >470 |
| 85 | >390 |
| 86A | >350 |
| 86B | >350 |
| 87A | >290 |
| 87B | >290 |
| 88 | >450 |
| 89 | >430 |

EXAMPLE 97

Various illustrative compounds synthesized in Examples above were tested for biological half-life. Compounds were incubated at a concentration of approximately 2 mcg/mL in a rat liver S9 preparation which was prepared according to standard procedures with minor modifications[1]. The reactions were conducted at 37° C. in a water bath and stopped by the addition of ice cold methanol at various times ranging from 0 to 20 minutes. Aliquots of the incubations were analyzed by high performance liquid chromatography (HPLC) for the compound of interest. The analyses were conducted on a Waters HPLC system consisting of a model 510 pump and a Wisp model 712 automatic injector. Waters C18 columns were used to perform the separations. The compounds were detected by UV adsorption. The mobile phases consisted of acetonitrile and sodium phosphate buffer (40 mM, pH 3.5); specific conditions were varied slightly for each compound. Concentrations of each compound were determined with time and the rate of metabolism was determined by analyzing the data using the CSTRIP program[2.]

[1] Subcellular Fractionation of Rat Liver. S. Fleischer and M. Kervina in *Methods of Enzymology*, Vol. XXXI, Biomembranes Part A, S. Fleischer and L. Packer Eds., pp. 6–41 (1974).

[2] A. T. Sedman and J. G. Warner, "CSTRIP. A Fortran IV Computer Program for Obtaining Initial Polyexponential Parameter Estimates.", *J. Pharm. Sci.* 65, 1006–1010 (1976).

Table II, below, sets forth the biological half-life of these illustrative compounds:

TABLE II

HALF-LIFE OF 12-METHOXYDODECANOIC ACID DERIVATIVES IN RAT HEPATIC S9 PREPARATION

| Example # | Half-life (Minutes) |
|---|---|
| 49 | 1.07 |
| 56 | 1.97 |
| 18 | 8.46 |
| 14 | 2.41 |
| 68 | 8.54 |
| 17 | a |

[a]Not detected at initial sampling time (ca. 5 min.).

The antiviral agents described herein can be used for administration to a mammalian host infected with a lentivirus, e.g. visna virus or the human immunodeficiency virus, by conventional means, preferably in formulations with pharmaceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one mg/kg/day of the active compound and generally in a range of about 100 to 1000 mg/kg/day. The preferable route of administration is orally in the form of capsules, tablets, syrups, elixirs and the like, although parenteral administration also can be used. Suitable formulations of the active compound in pharmaceutically acceptable diluents and carriers in therapeutic dosage from can be prepared by reference to general texts in the field such as, for example, *Remington's Pharmaceutical Sciences*, Ed. Arthur Osol, 16th ed., 1980, Mack Publishing Co., Easton, Pa.

EXAMPLE 98

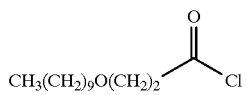

3-Decyloxypropanoyl chloride

The title compound is prepared by the method of Example 11 using an equivalent amount of 3-(decyloxy)propanic acid [the title product of Example 7] as a reactant instead of 12-methoxydodecanoic acid [the title product of Example 1].

EXAMPLE 99

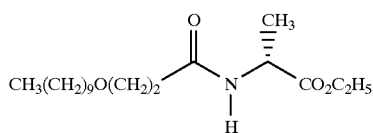

N-[3-decyloxy)proganoyl]-D-alanine, ethyl ester

The title compound is prepared by the method of Example 14 using an equivalent amount of D-alanine ethyl ester trifluoroacetate [the title product of Example 33] as a reactant insted of benzylamine, and using 3-decyloxypropanoyl chloride [the title product of Example 98] as a reactant instead of 12-methoxy-1-dodecanoyl chloride [the title product of Example 11].

EXAMPLE 100

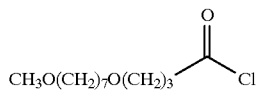

4-[(7-Methoxyheptyl)oxy]butanoyl chloride

The title compound is prepared by the method of Example 11 using an equivalent amount of 4-[(7-methoxyheptyl)oxy]-N-(phenylmethyl)butamide [the title product of Example 10] as a reactant instead of 12-methoxydocecanoic acid [the title product of Example 1].

EXAMPLE 101

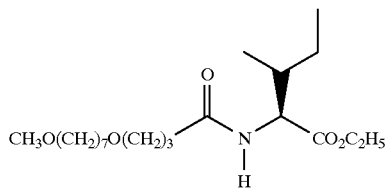

N-(4-[(7-Methoxyheptyl)oxy]butanoyl)-L-isoleucine, ethyl ester

The title compound is prepared by the method of Example 14 using L-isoleucine ethyl ester trifluoroacetate [the title product of Example 44] as a reactant instead of benzylamine, and using an equivalent amount of 4-[(7-methoxyheptyl)oxy]butanoyl chloride [the title product of Example 100] instead of 12-methoxy-1-docecanoyl chloride [the title product of Example 11].

EXAMPLE 102

The following compounds are prepared by methods analogous to methods described in the foregoing examples except that a sulfur heteroatom replaces an oxygen heteroatom in the fatty acid moiety of the compound, in which R is H, alkyl, aryl or arylalkyl, Y is amido, monoalkyl-amido, dialkyl-amido, monoaryl-amido, monoaryl-amido substituted with OH or halogen, diaryl-amido, and diaryl-amido substituted with OH or halogen, and in which the number of carbon atoms in alkyl are from one to eight and the number of carbon atoms in aryl is six.

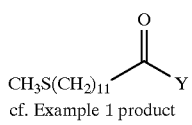
cf. Example 1 product

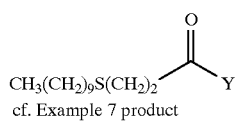
cf. Example 7 product

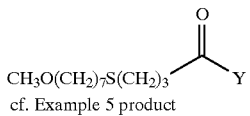
cf. Example 5 product

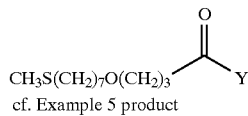
cf. Example 5 product

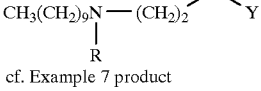
cf. Example 7 product

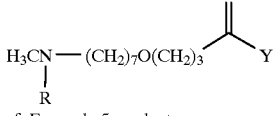
cf. Example 5 product

EXAMPLE 103

The following compounds are prepared by methods analogous to methods described in the foregoindg examples except that a nitrogen heteroatom replaces an oxygen heteroatom in the fatty acid moiety of the compound, in which R is H, alkyl, aryl or arylalkyl, Y is amido, monoalkyl-amido, dialkyl-amido, monoaryl-amido, monoaryl-amido substituted with OH or halogen, diaryl-amido, and diaryl-amido substituted with OH or halogen, and in which the number of carbon atoms in alkyl are from one to eight and the number of carbon atoms in aryl is six.

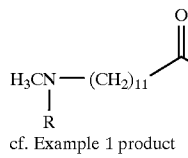
cf. Example 1 product

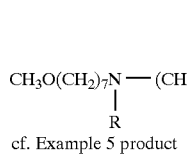
cf. Example 5 product

Various other examples will be apparent to the person skilled in the art after reading the present disclosure without departing from the spirit and scope of the invention. It is intended that all such other examples be included within the scope of the appended claims.

What is claimed is:

1. 4-[(7-Methoxyheptyl)oxy]-N-(phenylmethyl)butamide.

2. A method of inhibiting lentivirus in a host infected with said lentivirus comprising administering to said host a lentiviral inhibitory effective amount of the compound of claim 1.

3. The method of claim 2 in which the lentivirus is HIV.

4. A pharmaceutical composition comprising a compound of claim 1 in a lentiviral effective amount admixed with a pharmaceutically acceptable diluent or carrier.

* * * * *